(12) United States Patent
Campbell

(10) Patent No.: US 12,558,387 B2
(45) Date of Patent: Feb. 24, 2026

(54) MULTI-VIRUS ANTI-INFECTIVITY AND PRO-IMMUNITY ASSEMBLY

(71) Applicant: Farida Hanna Campbell, Maastricht (NL)

(72) Inventor: Farida Hanna Campbell, Maastricht (NL)

( * ) Notice: Subject to any disclaimer, the term of this patent is extended or adjusted under 35 U.S.C. 154(b) by 0 days.

(21) Appl. No.: 18/568,222

(22) PCT Filed: Jun. 7, 2022

(86) PCT No.: PCT/EP2022/065398
§ 371 (c)(1),
(2) Date: Dec. 7, 2023

(87) PCT Pub. No.: WO2022/258614
PCT Pub. Date: Dec. 15, 2022

(65) Prior Publication Data
US 2024/0269205 A1 Aug. 15, 2024

(30) Foreign Application Priority Data

Jun. 7, 2021 (EP) .................................... 21178040

(51) Int. Cl.
| | |
|---|---|
| *A61K 36/064* | (2006.01) |
| *A61K 9/68* | (2006.01) |
| *A61K 33/26* | (2006.01) |
| *A61K 38/16* | (2006.01) |
| *A61P 1/02* | (2006.01) |
| *A61P 31/02* | (2006.01) |
| *A61P 31/14* | (2006.01) |

(52) U.S. Cl.
CPC .......... *A61K 36/064* (2013.01); *A61K 9/0058* (2013.01); *A61K 33/26* (2013.01); *A61K 38/168* (2013.01); *A61P 1/02* (2018.01); *A61P 31/02* (2018.01); *A61P 31/14* (2018.01)

(58) Field of Classification Search
CPC .......... A61P 31/14; A61P 31/12; A61P 31/02; A61P 1/02; A23G 4/12; A23G 4/123; A23G 4/064; A61K 36/064; A61K 38/1732; A61K 9/0058; A61K 38/168; A61K 33/26; A61K 2300/00; A61K 8/1732; A23V 2002/00; A23V 2200/312; A23V 2200/324; A23V 2250/1592; A23V 2250/21; A23V 2250/218; A23V 2250/546
See application file for complete search history.

(56) References Cited

U.S. PATENT DOCUMENTS

| | | | |
|---|---|---|---|
| 2010/0255063 A1 | 10/2010 | Anderson et al. | |
| 2017/0196921 A1 | 7/2017 | Embree et al. | |
| 2021/0038664 A1 | 2/2021 | Legge | |

FOREIGN PATENT DOCUMENTS

| | | | | | |
|---|---|---|---|---|---|
| JP | 2005095178 A | * | 4/2005 | ......... | A61K 31/7052 |
| WO | WO-2005115341 A2 | * | 12/2005 | ............. | A61K 9/127 |
| WO | 2019023555 A1 | | 1/2019 | | |

OTHER PUBLICATIONS

Sharma et al., Development and Characterization of Gastroretentive High-Density Pellets Lodged With Zero Valent Iron Nanoparticles, Journal of Pharmaceutical Sciences, 107, 2663-2673, 2018. (Year: 2018).*

* cited by examiner

*Primary Examiner* — Lezah Roberts
(74) *Attorney, Agent, or Firm* — FRESH IP PLC; Michael H. Anderson

(57) ABSTRACT
The present invention relates to a method for a chewing-gum based mitigation of virus-related disease spread and pre-immunity activation based on disruption of syntrophic methanogenic processes in the oral-, shared oronasal and orotracheal microbiome. The invention provides a chewing gum composition comprising a methylotrophic yeast, preferably *Komagataella phaffii*; a plant lectin, preferably phytohaemagglutinin; and/or iron particles, preferably zerovalent iron particles.

15 Claims, 5 Drawing Sheets

Fig. 1.0
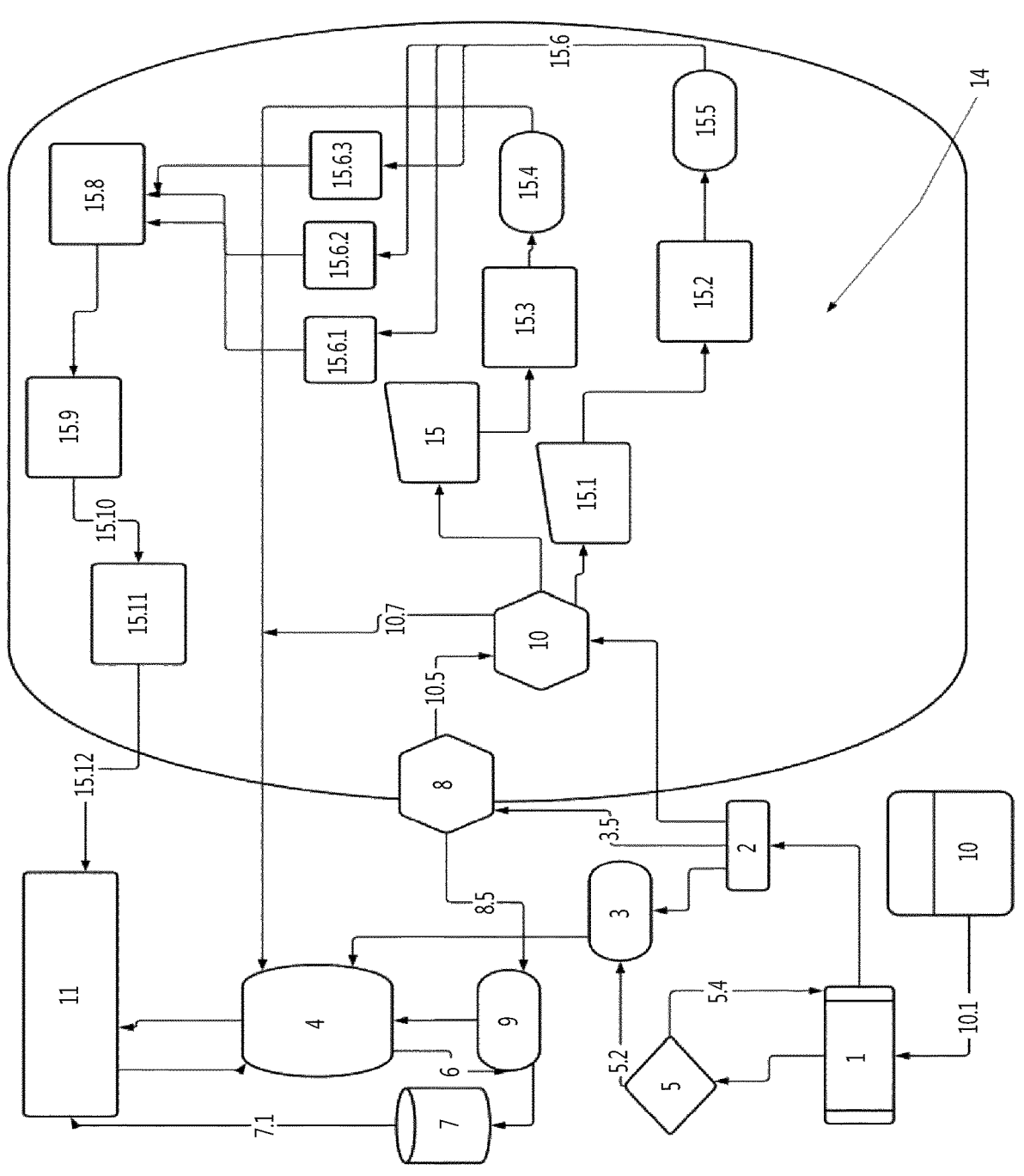

Fig. 1.1
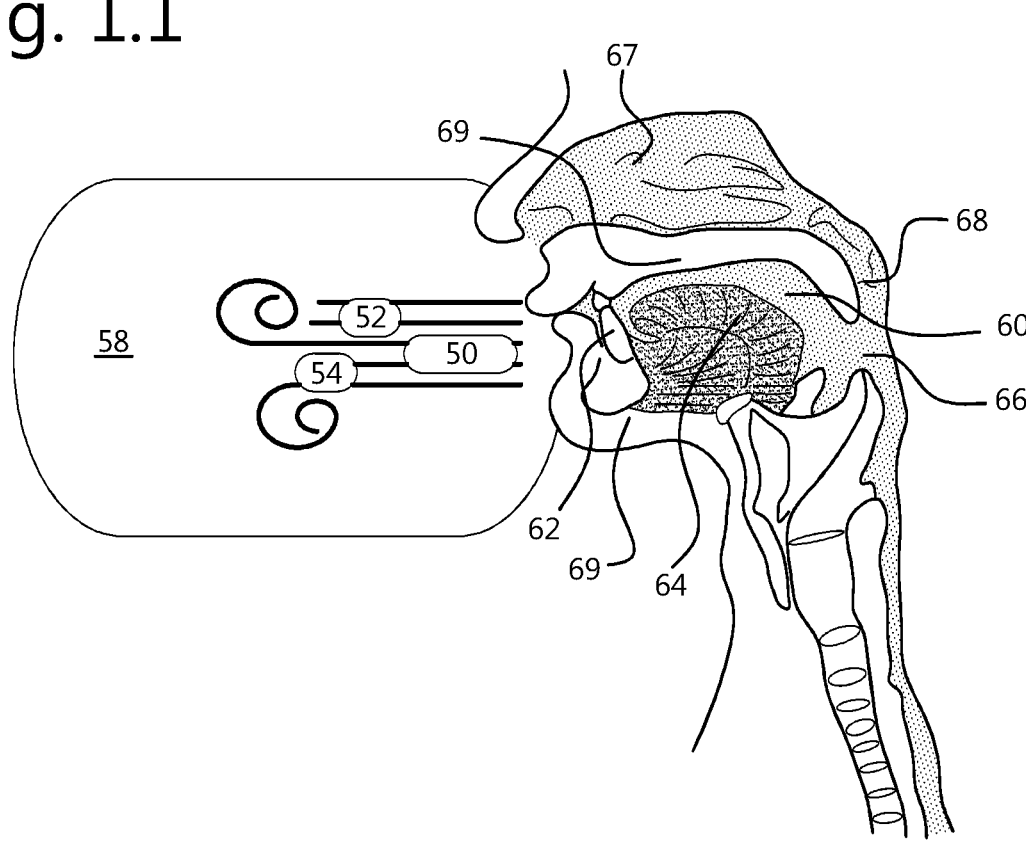
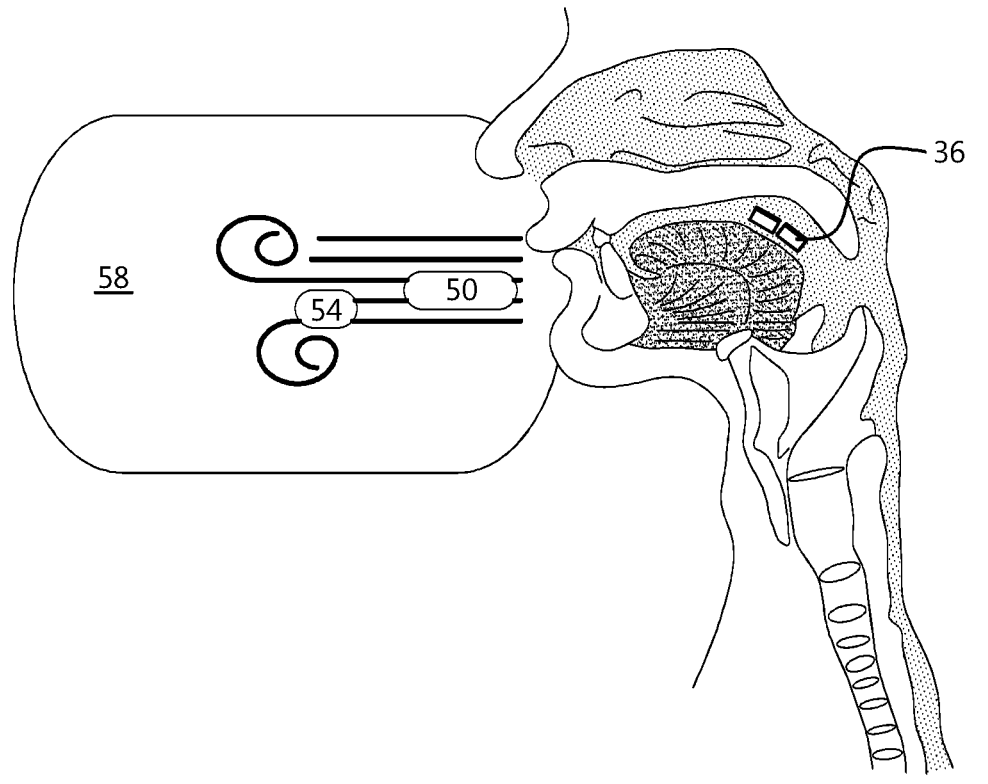

Fig. 1.2
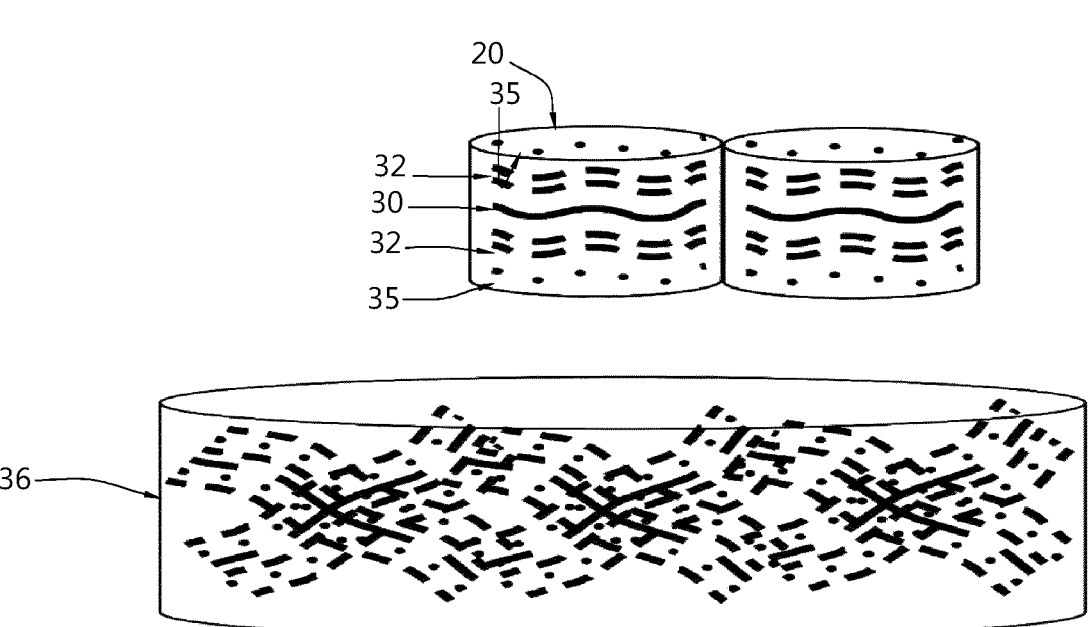

Fig. 2.0
Relationship of disclosure to the shared habitat reality
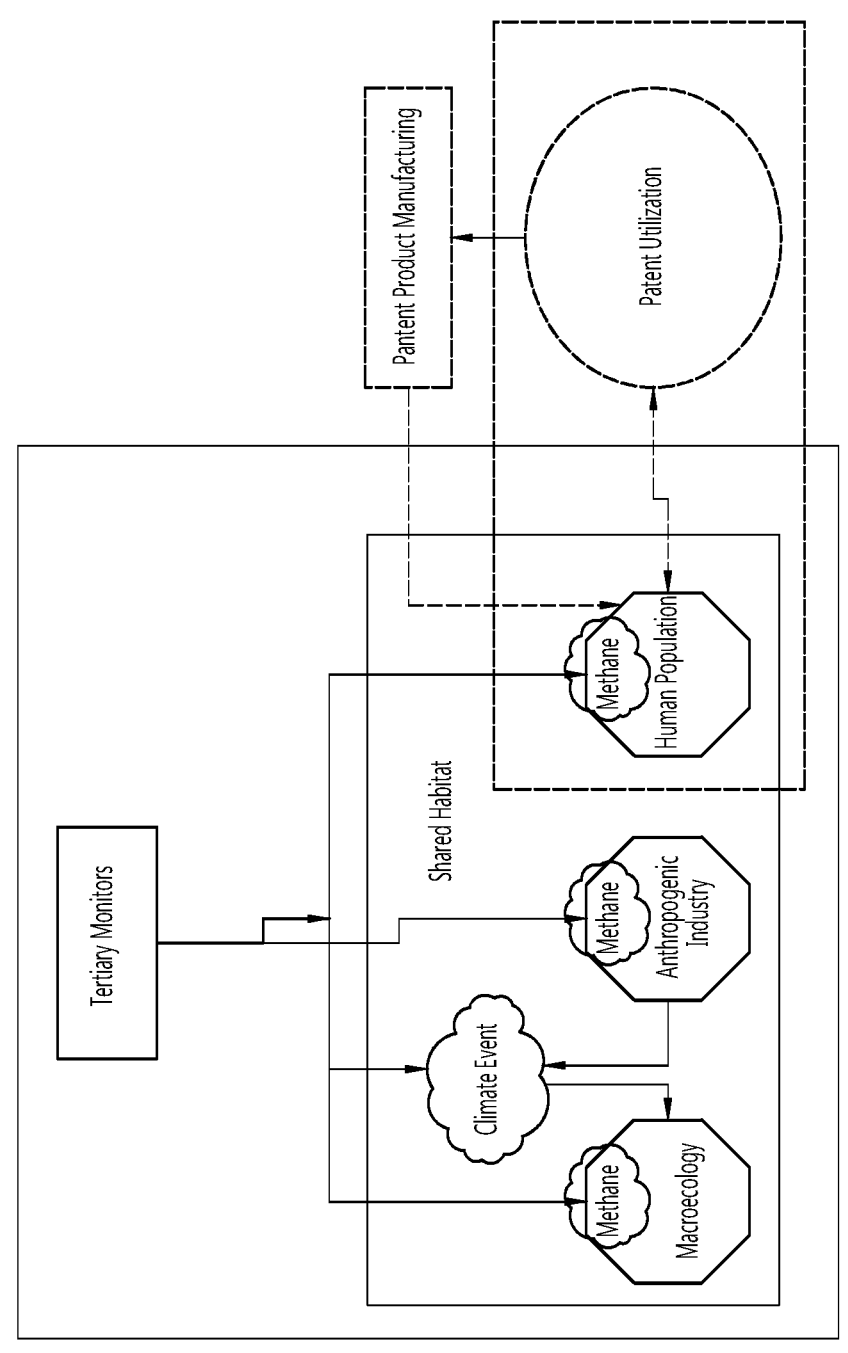

Fig. 3.0
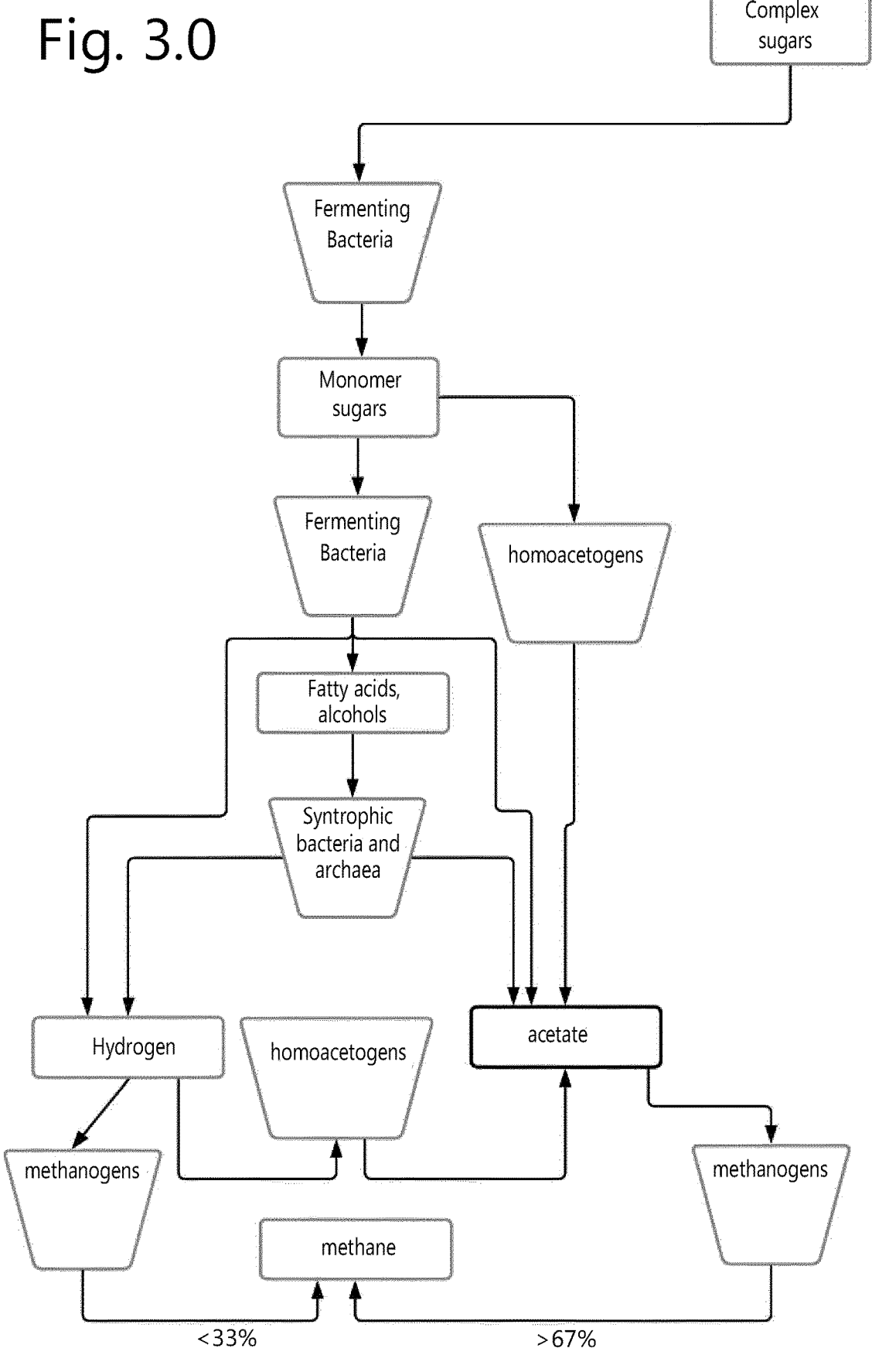

MULTI-VIRUS ANTI-INFECTIVITY AND PRO-IMMUNITY ASSEMBLY

TECHNICAL FIELD

The present disclosure provides a method for a chewing-gum based mitigation of virus-related disease spread and pre-immunity activation based on disruption of syntrophic methanogenic processes in the oral-, shared oronasal and orotracheal microbiome.

BACKGROUND OF THE INVENTION

Infective-disease renders humans infectious where and when volatile saliva-breath particles carry such lifeforms that render pathogenic disease outcomes in other humans. Transmission in the ambient environment means the delivery of infectious particles in the shared air, in soil and any surface media including skin that may come into contact with the humans.

It is an object of the present disclosure to reduce the risk of transmission of infective-disease, in particular to reduce the risk of future pandemics.

SUMMARY OF THE INVENTION

There are three components to the disclosure's method:

In the first part, the goal represents the assessment of the particular virus genome that emerges to cause an epidemic or pandemic outbreak. This is done via the thermodynamics of a climate-change extreme event, such as drought, in a given habitat which triggers a pathogenic-related general stress response in virus symbionts to infectious disease, the archaea- and protobacteria-targets found in the microbiome of human oral cavity and related to zoonotic exposure to that habitat's dominant species, whether or not such a dominant species includes natural wildlife or domestic livestock or both.

In the second part, the particular assessment of the size and duration of the outbreak is described indirectly as a measure of the rate of resource-consumption by that dominant species. The emphasis is on characteristics of the outbreak from the perspective of a virus species whose efforts are meant to ensure the survival of all biodiverse species in a post-stressed habitat by infection. Infection ensures breakdown of the immediate host (the symbionts) but, it also results in delivering genetic "wisdom" to the host that receives genetic survival information about the new environment via the GSR expressions of—and by the symbionts who share the host's oral cavity parasitically. To do so, this virus-infection relationship-event is described as the resolution of thermodynamic energy in equations that use the canonical conjugates for energy measurements converted into Hamiltonians. The non-uniform jurisdiction of infectious outbreaks depends on any methanogenic/methylotrophic types of virus-sustaining ecologies within the host's oral cavity and gastrointestinally, too. And in the product, a chewing gum is described with key ingredients to dephase the strength of the virus multiplication on behalf of both stimulating pre-infection immunity and by eliminating the infectivity-enabling targets of the oral cavity prior to infection within gastrointestinal tract; it also decontaminates breath as an anti-methane bactericidal product.

In this regard, the present disclosure provides for a composition, preferably a chewing gum, comprising:

a methylotrophic yeast, preferably *Komagataella phaffii*, most preferably provided in an amount of between $10^6$ and $10^{10}$ CFU;

a plant lectin, preferably phytohaemagglutinin, most preferably provided in an amount of 1-5 μg; and/or iron particles, preferably zero-valent iron particles, most preferably the iron particles are smaller than 50 nm and/or provided in up to 10,000 ppm in the composition.

Preferably, the chewing gum composition is a non-swallow chewing gum, most preferably a tube-shaped chewing gum comprising three intertwined tube-shaped strips, wherein a first tube-shaped strip comprises said *Komagataella phaffii*, a second tube-shaped strip comprises said phytohaemagglutinin, and a third tube-shaped strip comprises said iron particles.

As will be clear to the skilled person, the composition may further comprise (biodegradable) gum, oil compounds and/or synthetic latex. Preferably the chewing gum according to the present disclosure is for chewing after the last meal of the day and/or before sleep, preferably 1-2 hour before sleep.

The composition according to the present disclosure may be used for example for reducing susceptibility to virus infection and/or collecting virions, e.g. in a subject such as a human;

reducing methane level and/or methylmercury (MeHg) level, preferably in (human) breath and/or reducing the amount of methanogenic (proteo)bacteria, preferably as present in the oral cavity of a subject such as a human; and/or stimulate anti-viral immune response in a subject such as a human, preferably by activating T- and/or B-cell response.

The composition according to the present disclosure may also be used for example for preventing and/or treating antinuclear and/or antinucleolar antibodies disorders related to PASC (Post-Acute Sequelae of SARS-CoV-2 Infection) also referred to as long-Covid symptoms. Accordingly, the composition according to the present disclosure may also be used for example for preventing and/or treating PASC. Also, the composition according to the present disclosure may be used for preventing and/or treating neurological condition or any post-acute sequalae e.g. of MeHg pathogen related neurological impairment caused by at least one single infection event, whether of SARS and/or non-SARS virus/pathogen.

The use herein may comprise a use in a method of treatment, e.g. a therapeutic method of treatment. For example, the composition according to the present disclosure is suitable for use in (therapeutically) reducing susceptibility to virus infection and/or collecting virions, e.g. in a subject such as a human. In addition or alternatively, the composition according to the present disclosure is suitable for use in (therapeutically) reducing methane level and/or MeHg level, preferably in (human) breath and/or reducing the amount of methanogenic (proteo)bacteria, preferably as present in the oral cavity of a subject such as a human. In addition or alternatively, the composition according to the present disclosure is suitable for use in (therapeutically) stimulating an anti-viral immune response in a subject such as a human, preferably by activating T- and/or B-cell response.

Preferably, the methane level in breathe is established using a (commercially available) gas chromatograph and/or the hydrogen and methane breath test, which the skilled person is well familiar with. Preferably, the activation of the T- and/or B cell-response is established according to a peripheral blood mononuclear cell (PBMC) proliferation assay, more preferably according to the protocol described in the Examples.

The methanogenic (proteo) bacteria as mentioned above may be one or more of *Methanobrevibacter oralis, Methanobrevibacter smithii, Methanosphaera stadtmanae, methanomassiliicoccus luminiyensis, Methanobrevibacter arboriphilicus, Methanobrevibacter oralis, Candidatus methanomethylophilus alvus, Candidatus methanomassiliicoccus.*

Detail

Outbreaks of viruses-related disease are described according to thermodynamic characteristics leading to the evolution of virus-related species. The evolution of a new species is regarded relative to the principles of virus ecology, and targeting biodiversity offspring sustainability in its native habitat(s), immediately after—or just upon an extreme environmental threat or stress condition. And so, sustainability means that viruses (majority RNA-virus) will infect rapidly any of the dominant species which impact the distribution of available resources and to ensure the nutrients to non-dominant species. The virome transmits genetic instructions during infection which codes for species' improved resistance (immunity) in changing environments (alternative realities) that result from the events. And so this disclosure derives the virus genome template according to the dominant species following meteorological tertiary-sourced evidence of a climate extreme event. Whether such extreme change is of natural or anthropogenic causes, this disclosure includes the stress response proteins of the methanogenic/methylotrophic symbionts to characterise the forecasted duration and location of outbreaks where such symbionts are integral to host (human) virus-infectiousness and virus multiplication, in the human oral microbiome. The purpose of doing so is to predict the logistics of human oral-breath sanitization with a chewing gum base that sanitizes breath from virion particles and that enables pre-immunity together with the proteins of the saliva. The sanitization is based on mechanical mastication of a non-swallow chewing gum base that has key pharmaceutical ingredients in it, including *Komagataella phaffii*, phytohaemagglutinin, and nanoscale zero-valent iron particles. Saliva that mixes with these gum-adhering active compounds collect virion and as well as methanogenic species, clearing unsafe and unhealthy human methane (*K. Phaffi*) that is the basis of subsequent proteobacterial relationships in virus infection of the human host, and of course, disease. During mastication, salivary proteins communicate vital information about the virus-threat exposure directly to the brain, instigating sensitive pre-immunity, including immune T- and B-cell respond sensitively to the new virus species. In addition, the use of a quantum circuit enables prediction of future virus genome according to that habitat for which pre-immunity timeliness by gum-chewers offers an additional public health gain advantage.

The result is therefore described as a preventative method against virus-disease spread by humans; a product that reduces human methane production; a product that recognises sustainability evolution and environmental threats.

In the following description and examples, a number of terms are used. In order to provide a clear and consistent understanding of the specification and claims, including the scope to be given such terms, the following definitions are provided. Unless otherwise defined herein, all technical and scientific terms used have the same meaning as commonly understood by one of ordinary skill in the art to which this invention belongs.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements.

The indefinite article "a" or "an" thus usually means "at least one".

DETAILED DESCRIPTION OF THE INVENTION

Specifically, this disclosure involves:

A. Archaeal targets of human oral cavity: *Methanobrevibacter oralis plus, M. smithii Methanosphaera stadtmanae methanomassiliicoccus luminiyensis Methanobrevibacter arboriphilicus M. oralis, Ca. methanomethylophilus alvus Ca. Methanomasslliicoccus* where present in the human oral cavity;

B. Proteobacterial targets of human oral cavity, whose main physiological groups include bacterial phyla Proteobacteria, Bacteroidetes and Actinobacteria, Fusobacteria, and especially dominant genus *Streptococcus, Haemophilus, Neisseria Prevotella, Veillonella*, and *Rothia* which vary in percentage from individual but which are listed in their greater to lesser abundance in generally all modern humans in the research[1]

C. DNA and RNA viruses which emerge and evolve in response to abiotic triggers in the environment or habitat ecology that humans share and/or industrially exploit and that prey or graze on bacteria in humans that are:
   (i) acidophilic, aerobic iron oxidizers;
   (ii) neutrophilic, aerobic iron oxidizers;
   (iii) neutrophilic, anaerobic (nitrate-dependent) iron oxidizers; and
   (iv) anaerobic photosynthetic iron oxidizers.

Pandemic virus related disease follow drought. Drought triggers bacterial General Stress Response (GSR) and this response is activated literally globally. GSR is a process that includes a GSR-activating phosphorelay that is countered by a PhyR-NepR Binding to help the target of pandemic-related viruses, i.e., the proteobacteria survive multiple abiotic stress events, including extreme pH, temperature, salinity, radioactivity, industrial events and more.

GSR is responsible for the new or sudden increase in energy sensing behaviours in bacteria that helps bacteria within the syntrophic relationship migrate to locations which are not nutrient-poor that are caused by drought (motility), and into locations which are visibly nutrient-rich and abundant such as alternative habitats that offer the nutrients that can potentially defy the drought. This includes infection of dominant species in today's increasing agricultural habitat that hosts livestock and non-nomadic humans in regions of drought.

Bacteria motility is part of the spread phenomenon observed in pandemic outbreaks. Motility is part of the GSR-behavior, and includes very sensitive energy-state sensing of the environment. It is invoked by genetic signaling properties that underpin the entire GSR behavior, in order to help the bacteria migrate away as quickly as possible from a habitat faced with nutrient limits and threats to its future survivability. Motility also describes conversion of healthy aerobic to anaerobic species in the haemocel of some insects following drought, becoming pathogenic to wildlife such as bats that rely on insects in the so-called ecological "food chain". For example, motility such as swimming and fluids ranges on average between 1 to 1000 micrometres per second, representing conditions where the rate of is faster than the bacterium can find it versus where the threat of survival requires superior chemically spatial sensitivity and orientation, the maximum motor rotation rate, length and number of flagella. In Mitchell and Kogure (2006), bacteria become constrained when located less than 10 micrometers from a surface and cells swim parallel or escape from surfaces more than 20 nanometres away or in parallel to the direction of their travel; cells greater than 10 micrometers away do not feel a surface[2].

Growth of extremophile methanogenic archaea species contribute to the drug-resistant anaerobic proteobacteria symbionts that exchange methane and CO2 together, in humans. Archaeal methanogens arrive in exceptionally high numbers in industrial livestock meat-operations. The domain includes non-varied short-lived monospecies of pork and cattle herds for the production of related salted products that are distributed for human mass-consumption as human food. The conversion of methane by their sym- bionts such as *Prevotella, Streptococcus* and other bacteria which normally are found in the gut and hindgut of live- stock, including chicken, and which provide the tempera- ture-dependent H2 and other nutrients, results in prolific methanogenic archaeal growth *plus* the arrival of either DNA or RNA viruses (positive and negative, short and double stranded) based on killing the dominant host that threatens the nutrient availability of less dominant hosts or the alteration of the hosts whose survival is threatened because of the loss of resources in the extreme-event, such as loss of water during drought.

Viruses have Finite Length RNA/DNA Segments that Encode Proteins.

The steady-state solution represents the outbreak of a new virus species which will have evolved to maximize matches with the genome of the GSR-representing dominant host species, described above. Mutations of the virus include new arrays of matches to some target receptor of the host described by the GSR-expressing species, likewise. And so, the virus mutations each have an individual probability of successfully crossing the host-immunity barrier and each probability can be used to score the relative fitness of the virus in its environment.

1) Low temperature viruses with a high match
  2) Very high temperature viruses, viruses of any match are able to infect and reproduce Increased temperature represents increased percentage of viable virions in a new species distribution.

Therefore, the thermodynamic temperature for the system provides energy for the viruses whose genome is described by the array of evolving mutations to match the thermody- namic temperature of the host. The fitness of any virus represents a measure of how well the A, C, G, and U/T in the virus genome matches the host's genetic sequence in order to bind to its receptors.

Each bacterial species responds biphasically to altering concentrations of nutrient availability during climate change. In this disclosure, mapping refers to thermodynamic gradients where virus emerge to breakdown dominant spe- cies that consume excessive nutrients at the expense of nutrient supply availability to diverse species. And so, niche monitoring may facilitate measurement rates of motility to include in the relevant equations reported in this disclosure prior to an outbreak manifestation. Other rates, such as multiplication of viruses relative to syntrophic bacterial growth rates can be obtained from wastewater samples.

General Method

The end result of this disclosure is a chewing gum, FIG. 1.2, that contains variable viral removing, anti-viral, anti- methanogenic and anti-bacterial elements in any suitable gum base, derived from biodegradable tree gum, oil com- pounds or synthetic latex plastics. The ingredients include *Komagataella phaffii*, nanoscale zero valent iron particles, and phytohaemagglutinin (32, 35, 30, respectively).

The gum can be produced by a competent manufacturer and distributed to human populations that are stationary in the shared habitat of the source of an outbreak trajectory, which is predicted from the stress responses of proteobac- teria to environmental stress, namely climate change extremes such as drought (FIG. 2.0) and availability of nutrients, particularly as methane. The gum's mastication (36) helps to sweep, clear, trap and retain virion particles and their methanogenic/methylotrophic syntrophic nutrients from within the oral cavity following gum mastication (36, FIG. 1.2) with the aid of the tongue (66), saliva in the mouth (60) and abrasion between the ingredients and surface structures of the mouth cavity including teeth (62) and roof or lower jaw (69). Breath that is exhaled (50) which nor- mally contains methane (52) and CO2 (54) gases is pre- vented from discharge in the shared ambient air (58). This prevents the risk of mutual infectivity because methane is one of the nutrients detected by motile proteobacteria and it is mainly produced by the archaea in the oral microbiome that threaten infectivity leading to disease and disorders, and the resistance of the bacteria to anti-bacterial pharmaceuti- cals in previous pandemics. Thus, with mastication of the gum, the archaea organisms are cleared by the properties of its pharmaceutical ingredients while at the same time these ingredients enable healthy microbes to remain stable.

In FIG. 1.0, and in Clause 1, tertiary monitors (10) for climate and landscape or environmental monitoring satel- lites or ground mass spectrometers provide the general image local climate extreme event mapping images that are converted into quantum images that are used to evaluate the virus genome.

In FIG. 1.0, the minimum steps to build the quantum images that describe a path of spread and the genome are shown. The gum merely targets the proportion of pharma- ceutical ingredients to reduce the negative thermodynamic gradients in a habitat that relies on viruses to re-distribute nutrients to all of its diverse species. The use of a quantum circuit determines alternate realities represented by the genomic evolution of new virus species *plus* the changes in the symbionts' behavior due to the change in environment in order to cause pathogenic disease outbreaks (Clause 1.2.2.4).

The data collected (10.1) in Clause 1 includes changes in temperature, pH (acidity/alkalinity) and moisture rates of variation, such as supplied from real-time tertiary monitor- ing sources (10). The data is calibrated against a ground- state stable climate comparison so that the ideal output of the data is a map image (1) of the habitat that shows contour lines and colourized topological features of the habitat.

In Clause 2, quantum circuits (3) are used to convert the map data (10.1) according to the contours or the scale of colour intensity. This process is continued (5.4) for the duration of an outbreak where the habitat is shared with high human populations (2) and/or the infectivity potential is a measurable concern (Clause 1.2.3.2).

The quantum circuit (3) preferably contains a sufficient number of processing qubits and/or future quaterbits so that the gates produce a new image that maps spread, based on the same thermodynamic gradients wherever humans are hosts of the same GSR-behaving symbionts (5.2).

It is preferred to determine the future emerging virus from the genome of the dominant species (10). This is explained by the steps in Clause 1.2.3. The infectivity (10.5) to humans is explained in clause 1.2.3.2.

On the right side of the future, is the evaluation of the anti-outbreak, anti-virus component which includes the chewing gum whereby mastication of the gum (20) and its incumbent pharmaceutical ingredients of *Komagataella phaffii*, nanoscale zero valent iron particles, and phytohae-magglutinin (32, 35, 30, respectively in FIG. 1.1) will stimulate the immune system prior to infection as well as remove the infectious risk within the oronasal (68, FIG. 1.2) and orotracheal (69, FIG. 1.2) passage way, plus to sanitize human breath in the mouth (60, FIG. 1.2) against pathogenic syntrophic symbionts inherent to disease spread in ambient shared air (58, FIG. 1.2). Human host time of infectivity occurs when the ambient environment of the oral tissue pH drops. And so, ideally, the chewing gum must be used to provide the anti-pathogenic sanitization at that time. Tests of the chewing gum for its anti-infectivity maximum performance may be based on the assembly of ingredients, response and collection of pathogens that become active or inactive according to the pH of the oral cavity.

Specific Method

In the general method, it was described that a location with a climate stress that threatens resource distribution and availability to sustain the habitat's diverse spectrum of living organisms, the habitat must be evaluated from the perspective of the virus to reduce the dominant species population and/or threat to that resource availability (8). It was stated that this is the method to determine which species will face the most pathogenic forms of population reduction (disease outbreak) and which species will face the greatest survival-related strengthening genetically by the virus(es) (8.5) wherever the species is a host to the same syntrophic microbiome species.

The dominant species in a given habitat is portrayed collectively in thermogradient negative variations that emerge from the calculations in the corresponding clause, whilst the non-dominant species the least negative variation and likely positive variation (9). These variations are then mapped in images from the quantum circuit (7) so that they are re-converted into contour lines or colour-keys (7.1). The map of decreasing negative gradient points to virus-outbreak spread direction (11).

There are alternative methods for producing the outbreak spread, one as given in variations of macroecological thermodynamic responses by the virus to preserve sustainability, and based on Clause 2 quantum image development. The Clause 2 version is used in the process of building the measurements of chewing gum for manufacturing. But the Bohmian trajectories given in Clause 3 may also be used. In all cases, each quantum circuit throughout the disclosure may be designed by an algorithm to parallelize the processing of information as much as possible. This allows the maps to be joined from habitat to habitat in the forecast of spread over continent.

The virus infectivity vulnerability (3.5) is a function of host-population size and the degree of consumption by the population (2) that is contrary to the urgent need for recovery of the environmentally-stressed habitat area-range.

Multiple quantum circuits per habitat can be self-assembled in what can be called a quantum disease circuit that reports otherwise unpredictable virus outbreaks (11) from zoonotic sources. These circuits are continually correlated to the macroecological thermodynamic changes following from an environmental stress in clause 1.2.

Contour maps based on these thermodynamic gradients give a picture of the orientation and direction of outbreak threat from a zoonotic source(s) (11) given in clause 3.1.3.1.

Contours are important to identify where a vulnerable human population is stationary. These populations should be evacuated immediately from a stressed-habitat that relies on virus ecology to restore the distribution of metabolic resources sustainably. Where and when evacuation of humans is not possible, then the manufacturing of the chewing gum product applies.

If so, the quantum circuit may be established so that suitable amounts of the anti-outbreak chewing gum generates the equal counter-effective proportion of the thermodynamic gradient reversal of (9).

For the chewing gum development, the ideal method determines the available symbionts for virus species grazing within the oral microbiome. This means it is important to determine the archaea emergent (15.1) for the kind of extreme climatic conditions (1) and the methane level produced (15.2). Then, one uses the established gut bacteria (15.3) of the dominant species, recalling that the dominant species is the species that consumes the greatest proportion of habitat-available resources (water, nutrients, etc) and in which the proteobacteria survival and multiplication is sustainably the easiest and highest, thermodynamically. The interaction rate of the virus multiplication with these symbionts in the oral cavity may also be used (15.4) to glean the required chewing-gum daily frequency. The threat of an outbreak is related to the threat of survival that was expressed as a GSR-response by these microbiotic species. The increased GSR, the increased rate of spread. The increased threat to metabolic nutrient supply for the essential survival of all habitat diverse species, the more aggressive the decimation of the dominant species by the virus in the earliest time (15.5). For a minimum spread rate that is greater than zero, obtain the motility rate of those bacteria (15.6.1) and the multiplication rate in the presence of methane when motility has ceased in a new host (new point of supply, new human victim, etc) (15.6.2). On the map (4), identify all adjacent sources of nutrients according to change in thermodynamics for the habitat given in the clauses (15.6.3).

Using the rate of protobacteria motility and the (15.6.1) and the identification of the densest sources of nutrients (15.6.3) on the image (4), determine the minimum time by the species to reach the new nutrient-dense locations (15.8). At the new nutrient rich locations (15.8), calculate the multiplication population that will emerge by multiplying this rate with the series of reductions of the nutrient (15.9). Where this series of reductions is eliminated by anthropogenic industrial replacement, such as livestock increased product, make the corresponding thermodynamic factor of adjustment. Now, use the multiplication population (15.9) to determine the proportional virus growth (15.10). Human infectivity rate statistics (clause 1.2.3.2.4) may be used to plan early-protection of immunocompromised persons in the location of outbreak trajectories. The duration of an outbreak is ecologically strategically tied to the nutrient limits of the habitat following an environmental extreme. And so the increased speed of spread by multiple virus variants represents multiple occurring climate stresses and their nutrient limits, accordingly. If so, poly-virus pandemic outbreaks will still be disrupted by the basic architecture of the assembly of anti-methanogenic ingredients in the chewing gum and these will represent the pursuit of limited nutrients from mixed habitat-related GSR-behavior genetic signaling.

This means, the goal of the chewing gum to be produced by a manufacturer preferably equals the counter-thermodynamic proportionally of the virus outbreak. Such an outcome artificially nullifies the visibility of those humans who are chewing gum users (consumers) to the virus seeking to graze on the infective symbionts within the human's oral microbiome. Recall that these symbionts are the ones expressing a GSR-behaviour. The invisibility to virus outbreak is the result of active sweeping out of methanogenic-syntrophic events in the oral cavity during mastication—even while such interrelationships may continue in the gut or other microbiomes of other dominant species in the surrounding shared habitat; and, and actively triggering pre-infection saliva-based brain-immunological and cellular immunological sensitivity to the concentration of the virion particles in the gum itself. The symbionts are therefore removed along with the virus particles trapped inside the gum prior to risk of ingestion into the small intestine of the gastrointestinal tract where such symbionts would continue to generate highest probabilities of infection and for which vaccination triggers the risk of increased post-infection virus-resistance within the host, leading to vaccination temporariness. It is worth pointing out that the gum prevents virus-archaeabacteria exposure to the small intestinal wall, where the gut anaerobic environment facilitates their multiplication in faeces. The methane-related damage to the wallenables virus distribution to blood, and to reach other regions of the lower respiratory organ system, the peripheral nervous system and to bypass the blood brain barrier with the latter and to reach the brain. And so, the use of the chewing gum is wholly a preventive measure, owing to its ability to sweep and clear the methanogenic and methanotrophic symbionts out of the oral cavity (mouth) directly, reducing human methane-byproduct disease risks accordingly.

Clauses

1. From a suitable scientific tertiary resource (e.g., European Copernicus Satellite or other tertiary source)

1.1. Collect geotimestamp (coordinates and time of day) specifications of drought or extreme climate-change parameters that can be physically converted into corresponding thermodynamics of the ambient environment for a corresponding event. This includes temperature, pH, and precipitation, moisture vs dryness, and related events at significant light-varying times of the day.

1.2. A future new evolution of zoonotic virus species that is predicted according to significant macroecological thermodynamic comparisons of the general stress response of the microbiota that become motile and/or pathogenic in the dominant living species in a given habitat that is threatened by a climate-extreme event such as drought; that is, 1.2.1. Use existing nautical, military or environmental-resource mapping coordinates to Identify the event-center and its map-coordinates for the habitats that are directly located within the drought or extreme-climate change event during its initial onset and for the duration of the event 1.2.2. List the dominant species of wildlife in the event-location 1.2.2.1. Identify and select the dominant wildlife or agricultural species that is dominant according to that which is the largest and greatest nutrient consumers for the event-habitat.

1.2.2.2. Identify the DNA genome (oligonucleotide) or as an alternative the G-quadruplex or significant RNA of the dominant nutrient-consuming species in the event-habitat by any suitable methods, whether by direct scientific cellular tissue laboratory analyses or via existing published records that can identify the parameters of describing a pattern of genomic DNA protein expressions 1.2.2.3. Use the information of 1.2.2.2. to establish outstanding General Stress Response (GSR) related RNA polymerase proteins SigmaB in any Gram-positive bacteria in the soil or wastewater; and, an ECF (extracytoplasmic function) sigma factor in alphaproteobacteria GSR. Regardless of how the response starts, such as with the direct or indirect activation of PhyR or its orthologues by signal-integrating histidine kinases or other members of the same the HWE/HisKA2 family[3], in the RNA polymerase redirects transcription which initiates and sustains the GSR-activation by binding with EcfG, and is referred collectively as the GSR-activating Phosphorelay[3] and compare the measurement of levels of the parameters that describe the response variations before-, during and following the drought or extreme climate change event.

1.2.2.4. For the dominant consumer species identified in 1.2.2.1:

1.2.2.4.1. Identify its corresponding internal or external microbiome species involved in greatest rates of environmental-interactivity as part of syntrophic respiration between syntrophic archaea, proteobacteria and other lifeforms including viruses: the skin microbiome, and oral-ingestive and gastrointestinal pathway and, if applicable, any specialized mobility morphology.

1.2.2.4.2. Now, refer to this dominant consumer species as the point source of accumulation and release of microbiome related methane gases to the environment for which its microbiotic proteobacterial species are critical to the evolutionary relationship trigger of a pathogenic virus to humans that may be exposed to similar or identical species when such humans share the habitat with the dominant consumer species.

1.2.2.4.3. Once again, identify the proteobacterial and archaeal DNA genome (oligonucleotide) or as an alternative the G-quadruplex or significant RNA, whether by direct scientific cellular tissue laboratory analyses or via existing published records that can identify the parameters of describing a pattern of nucleic acid protein expressions 1.2.2.4.4. For the species in 1.2.2.1 and 1.2.2.4.1, use the nearest neighbour method or any scientific research tools available that are suitable to sample and report the median thermodynamic temperature, fraction-bindability and related parameters for the species' DNA and RNA. The nearest neighbour data or a thermodynamic algorithm may be obtained from published references such as Huguet et al (2017) 4 including for the derivation of enthalpies and entropies based on characteristic melting Temperature of the DNA nucleic acid bonds.

$$\Delta h_i = \Delta h_2^s$$
$$\Delta s_i = \Delta s_r^\circ + \frac{m_i}{T} \ln\left[Mg^{2+}\right]$$
$$\Delta g_i = \Delta g_i^\circ - m_i \ln\left[Mg^{2+}\right]$$
$$\Delta h_{AT} = \Delta h^\circ_{AT}$$
$$\Delta s_{AT} = \Delta s^\circ_{AT}$$
$$\Delta h_{CG} = \Delta h^\circ_{CG}$$
$$\Delta s_{CG} = \Delta s^\circ_{CG}$$

where $\Delta h_i$, $\Delta s_i$ and $\Delta g_i$ are the enthalpies, entropies and free energies of the eight independent NN motifs ($i$ =AA/TT, AC/TG, . . . ); $\Delta h_i^\circ$, $\Delta s_i^\circ$, and $\Delta g_i^\circ$ are their values at standard conditions ([Mg2+]=1 M, T=25° C.), and $m_i$ are the Mg2+ salt corrections pre-factors. $\Delta h_{AT}$ ($\Delta h_{CG}$), and $\Delta s_{AT}$ ($\Delta s_{CG}$) are the enthalpy and the entropy of the AT (CG) initiation factor; they are taken equal to their values $\Delta h_{AT}^\circ$ ($\Delta h_{CG}^\circ$), and $\Delta s_{AT}^\circ$ ($\Delta s_{CG}^\circ$) at standard conditions.

1.2.2.4.5. Repeat 1.2.2.4.4 but instead, select each DNA genomic sequence for those species in their microbiome which had exhibited the lowest or no expression of GSR during the drought—and do so, for all and any species of bacteria or archaea or other entities (including fungi) within that host's microbiome, accordingly. This is done by laboratory scientific cellular sampling or by published references.

1.2.2.4.6. Measure the syntrophic rates of the microbiotic ecology:

$$v = \frac{v_{max} \times [S] \times (1 - \exp(\Delta G_{rxn}))}{K + [S] \times (1 + k_r \times \exp(\Delta G_{rxn}))}$$

where
$\Delta G_{rxn}$ is the thermodynamic energy available in the reversible reaction for a given set of substrate and product concentrations given by $$\Delta G_{rxn} = \Delta G_{rxn}^{0\prime} + R \times T \times \ln\left(\frac{\prod_i a_i^{m,i}}{\prod_j a_j^{m,j}}\right)$$

And where R is the gas constant, T is the temperature, a and m are the chemical activity and stoichiometric coefficient of each compound involved in the reaction, i and j are indices over products and substrates, respectively, and $\Delta G_{rxn}^{0\prime}$ is the change in free energy under biological standard conditions (1 M concentration of all solutes, 1 atm, 25° C., and pH 7), in Grosskopf and Soyer (2016)[5].

1.2.3. For the species in 1.2.2.1 and 1.2.2.4.1, the complement of this DNA reports the outstanding classification of the virus template and represents a significant proportion of what the virus RNA (drought) will strive to match in the new evolving virus while also expressing variations known as mutations in chronic reinfection of any human host that remains in a location that has the highest volume of nutrients required for the syntrophic species' metabolism and respiration.

1.2.3.1. Measure the thermodynamics of the complementary match genome (complementary DNA or RNA strand) by any state of the art method (for example, TEEM (Toehold Exchange Energy Measurement)

1.2.3.2. Establish the infectivity required by the virus through its multiplication by the following:

1.2.3.2.1. Refer to this as the maximum outbreak rate based on the maximum virus match ($f_b$=1000%) with DNA genome (oligonucleotide) or as an alternative the G-quadruplex or significant RNA of the target-host genome template described in 1.2.2.

1.2.3.2.2. The probability of match is conservatively projected to be 100% for product manufacturing and distribution purposes where, 1.2.3.2.2.1. the host contains a maximum likelihood for a volume of viruses to instantiate vulnerability to an virus-infection mechanisms and where, the human host is the one who bears living syntrophic-species in its oral microbiome or the host is the one who breathes or ingests particles of debris or moisture that are contaminated with the living syntrophic species in a natural way from shared air;

1.2.3.2.2.2. the virus multiplication naturally enables the predicted virus-species to reduce (kill) or alter (chronically infect) the host within the first infection 1.2.3.2.2.3. the purpose of the virus infection is to transfer the matching genome (RNA or DNA) and to use the host cellular machinery for multiplication in the host 1.2.3.2.2.4. The purpose of genetic transfer allows the virus to reduce the syntrophic species' rate of consumption of nutrients that are limited in a given habitat 1.2.3.2.2.5. And that the measurement of this process is multiplied for the entire host population. This represents the volume of total reduction thermodynamically required from would-be infected hosts who instead chew gum. This essentially means that the virus(es) are prevented from targeting gum-chewers, because there is no methanogenic/methylotrophic proteobacteria. The purpose of this calculation is to determine the amount of chewing gum pharmaceutical ingredients that will quell the total energy to a state in which the virus-evolutionary triggers (on behalf of global nutrient restoration and survivability of host-related offspring) is stopped.

1.2.3.2.2.6. That the volume of the product-users (chewing gum) must achieve this maximum work-threshold in order to be an effective prevention of virus-multiplication 1.2.3.2.2.6.1. Where the work threshold required to achieve prevention is based on the percent effectiveness achieved by a human user of the product (chewing gum) multiplied for a given number of humans in a population 1.2.3.2.2.6.2. Where the effectiveness of the chewing gum is per piece per an expected number of days following the chewing of a piece of the gum for a minimum fraction of an hour per day.

1.2.3.2.2.6.3. Where the effectiveness required in 1.2.3.2.2.6.2 determines the volume of chewing gum to be manufactured and distributed to the population used in the measurement of 1.1.3.2.1.6.1. based on the cumulative outcome of the pharmaceutical ingredients when used in a chewing gum that is chewed at a specific rate for a specific duration in the oral cavity of a human user. This rate and duration is determined in the following:

1.2.3.2.2.6.3.1. Obtain chewing gum base ingredients using hygienic standards into average human-user friendly size and divide into three sections.

1.2.3.2.2.6.3.2. For the total effectiveness required in 1.2.3.2.2.6.2, distribute the fraction of anti-infectivity as the sum of syntrophic disruption caused by each pharmaceutical ingredient in the following way:

1.2.3.2.2.6.3.3. Next, obtain *Komagataella phaffii* from scientific commercial suppliers and mix in the effective proportion that will reduce the methane-components of syntrophic exchange; it may be mixed in one of the one-thirds of the chewing gum volume based on the proportion required as calculated from 1.2.3.2.2.6.2.

1.2.3.2.2.6.3.4. Alternatively, if 1.1.3.2.1.6.3 is not known by the seller/supplier of K.

| specific methanol uptake rates of *K. phaffii* Mut– strains from published research[6]. | | |
|---|---|---|
| | 4 hours | 20 hours |
| $q_{MeOH}$(mmol g$^{-1}$h$^{-1}$) | 5.3-7.8 mg g$^{-1}$h$^{-1}$ | 5.09-6.51 mg g$^{-1}$h$^{-1}$ |
| Heat Transfer Rate (WL$^{01}$) | 5.1-17.5 | |

1.2.3.2.2.6.3.6. Require mastication of the gum throughout the day but, with at least double the quantity of *K. phaffi* in the gum, to be chewed before meals in general for 1-2 hours but, also to specifically require use of the gum after the last of meals in a given day so that the most severely vulnerable human hosts enjoy a maximum prevention of virus multiplication simultaneously with diurnal immunity repair processes that take place during sleep.

1.2.3.2.2.6.3.7. Obtain 1 to 5 µg/ml Phytohemagglutinin (PHA) from a certified pharmaceutical seller; this is a lectin extract from red kidney bean (*Phaseolus vulgaris*) skin or other source by standard chromatographic techniques, consists of only L-type subunits (iso-lectin L4, "leuko-agglutinin") and to be mixed in one of the one-thirds of the chewing gum volume.

1.2.3.2.2.6.3.8. Obtain a single particle nanoscale zero-valent iron particle (NZVIs) per one third of an average piece of chewing gum volume, where each particle is smaller than 50 nm or up to 10,000 ppm and to be mixed in one of the one-thirds of the chewing gum volume. This particle drives redox changes in the pathogenic-proteobacterial species that causes them to be detected by the saliva upon cell burst, and accumulate together with any virion particles in the sticky, tacky nature of the gum bolus. Together the bacterial pieces, the virion particle and the nZVI particle activate T- and B-cell wall immunological responses immediately due to the nature of the host's saliva-blood exchange, prior to the virus penetration of the human host and in association with the loss of multiplication opportunity in the presence of now-defunct proteobacteria.

1.2.3.2.2.6.3.9. The restriction to particle size may be altered based on toxicity limits studies that may be available to measure maximum particle number per chewing gum piece according to the daily exposure due to chewing frequency and potential risk of swallowing.

1.2.3.2.2.6.3.10. Roll each of the one-third sections into an appealing single unit section. This means that the *K. phaffii* and chewing-gum base can be mixed and shaped into a single tube-shaped strip, for example. Likewise this means that the nanoscale zero-valent iron (nZVI) particles and chewing-gum base can be mixed and shaped into a second single tube-shaped strip, for example and similarly, in another tube-shaped strip, the mix of Phytohemagglutinin (PHA) in and chewing gum. Finally, each of the tubes can be twisted together about one another into one unit and packaged securely in a suitable wrap at −25-40 degrees celsius. This product is defined as the consumible user-friendly product for chewing and in order to produce the effects of syntrophic disruption of the infective virus-archaea-bacterial relationship that is hosted in the oral microbiome and to the proportion and frequency that is critical to the prevention of virus multiplication based on the genome of the virus species that responds to a measure of environmental threat. This also means that the chewing gum may be included in distribution to human users of any age that can chew without swallowing each gum piece, according to the minimum required number of hours per day.

1.2.3.2.2.6.4. For variation, replace the chewing gum with fully-biodegradable gum ingredients, partially-biodegradable gum ingredients or synthetic bubble-gum latex-derived ingredients with a certified process of mixing available from commercial manufacturers.

1.2.3.2.2.6.5. For each product-label, provide description of the virus species that is prevented by its use. If possible, include the evolution classification categories according to scientific standards of virus classification.

1.2.3.2.2.6.6. For each product-user, provide instructed so that the product is disposed of in a joint soil-remediation and biodiversity-enhancing recycling facility that can provide the necessary shredding and mixing with other post-chewed gum pieces together in agricultural soil and critical industrial vegetation restoration areas.

1.2.3.2.3. To calculate the volume of chewing gum required to stop the spread rate 1.2.3.2.3.1. Establish the host-bacterial growth rate $\gamma$ by any model such as the Gompertz model described in (1991)[7]:

$$y = A\exp\left\{-\exp\left[\frac{\mu_m \cdot e}{A}(\lambda - t) + 1\right]\right\}$$

where A represents maximal growth rate value reached for a given species, obtained from any experimental-data literature or in specific laboratory determinations, and $\mu_m$ is the maximum specific growth rate obtained in a similar fashion, and e represents $e^1$.

1.2.3.2.3.1.1. Establish maximum spread rate based on the following parameters:

1.2.3.2.3.1.1.1. Obtain the ambient temperature of the environment in which the host remains (seasonal temperature) such as from local environmental weather temperature sampling stations 1.2.3.2.3.1.1.2. Factor the growth rate according to the temperature sensitivity of the bacteria species, such as for *Streptococcus* group A so that the pharmaceutical ingredients are increased in proportion with increased bacterial growth rate during lower temperature climate or seasons such as by (but not limited to) the following factor $$\mu_m = [b_1(T - T_{min})]^2 \text{(Ratkowsky 1)}$$

where $b_1$ is a Ratkowsky 1 parameter ($^\circ$ C.$^{-1}$ h$^{-0}$), and $T_{min}$ is the minimum temperature at which growth is observed ($^\circ$ C.) in Zwietering et al (1991)[7]

1.2.3.2.3.1.2. Calculate the spread rate based on humans based on volume of approximately 600 expelled respiratory droplets that would occur where a given droplet diameter is 5 $\mu$m to 2000 $\mu$m, where the maximum saliva-virion droplet dispersion occurs via talking (25 $\mu$m-50 $\mu$m diameter droplets), but also sneezing (~800 $\mu$m) and, are conservatively assumed to be in a uniform dispersion in the volume of air expelled by all humans ($V_g$~0.0005 m$^3$; and where the total volume occupied by droplets of different sizes in a given act of coughing or sneezing is $\Sigma_i N_i D_{s,o,i}$ where N is the total number of droplets of size $D_{s,o}$ and $V_{s,o}$ is the volume of such a droplet. And by using size distribution, the volume of saliva droplets from sneezing, coughing, coughing with covered mouth, and talking loudly is 59 ppm, 549 ppm, 361 ppm, and 263 ppm, respectively[8].

1.2.3.2.3.1.3. Calculate the ambient spread lifetime characteristics, starting from breath to settling time on an ambient surface within a shared environment, $\sigma_H/^2$ with velocity described by the Stokes settling velocity equation w=$(\rho_p-\rho_f)$ gD$_s^2$/18$\mu$ and $\int_0^{t_{settle}}$ wdt=$\sigma_H$/2 where $\sigma_H$ represents intermediate droplets approximately 30 $\mu$m in diameter and the characteristic droplet lifetime $\tau$ is established between model curves for evaporation and gravity-settling times $\tau$=min $\{t_{evap}|t_{evap} \geq t_{settle} \forall D_{s,o}\}$ affording the greatest probability of spread that is meaningful to the physical conduit of virion/bacterial pathogenic particles in the model analysed by Chaudhuri et al (2020).[8]

1.2.3.2.3.2. Establish the differential thermodynamic component of the evolution of saliva contamination of the ambient air (the infective spread rate) that includes the spread rate per human multiplied by the total number of humans that are the desired consumer-distribution endpoint or user-base such as a school group of children and adults, a clinical staff group, a public event who may be exposed to and subsequently also the targets of a newly evolved zoonotic virus (whose species has been determined in 1.1.2.2 and 1.1.2.3 based on Chaudhuri et al (2020).[8] again:

$$mC_{p,l}\frac{\partial T_s}{\partial t} = -k_g A_s \frac{\partial T}{\partial r}\bigg|_s + \dot{m}_1 h_{fg} - \dot{m}_1 e_l.$$

Where, $T_s$ is the saliva droplet effective temperature $$m = \frac{4}{3}\pi \rho_1 R_s^3$$

is the average instantaneous droplet mass
$A_s$=4$\pi R_s^2$ is the surface area of the droplet
$\rho_1$ is the density
$e_1$ is the specific internal energy of the saliva
$k_g$ is the average conductivity of air/gas surrounding the droplet $$\frac{\partial T}{\partial r}\bigg|_s$$

is the thermal gradient and convective heat transfer at the droplet surface, approximated to $(T_s-T_\infty)/R_s$ for an estimated aerodynamics in the ambient air of Nusselt number less than 0.1.

1.2.3.2.4. A crude estimate of the reduction requirement may be enhanced with any kind of evaluation using deVries species mutation related statistics.

2. Use an algorithm published in research related literature or commercial references to build a quantum circuit, such as an algorithm for a quantum circuit that comprises a sequence of quantum gates to simulate k-local Hamiltonians:

2.1. Use the circuit to convert images of the climate-event on habitat maps into quantum images.

2.2. Use a secondary circuit to map the direction and orientation of virus-outbreak in spread according to any thermodynamic variables and/or combination of measurements found in Clause 1.

3. Use the climate-change extreme event to predict the trajectory of outbreak patterns based on the following:

3.1. In another variation, it is possible to build a circuit-building processor such as with a cloud host provider that supports realtime quantum integrations such as commercial IBM Qiskit, to build a quantum simulator circuit directly of the proteobacteria with a thermodynamic model of the bacteria as particles on a outbreak trajectory given in Raeisi (2012)[9]:

3.1.1. Climate extreme 3.1.1.1. Collect data regarding temperature, soil pH and salinity, moisture and wind, and relevant parameters for radioactivity, alkalinity and frost parameter data from tertiary sources that include image data weather-monitoring and earth monitoring satellites into each climate-change extreme event)

3.1.1.2. Use an recursive generation algorithm for Hilbert scanning matrix to transform images into a drought event (or extreme reporting quantum circuit) in Hilbert-space such as described in Wang et al (2014)[10]in wherein the images are quantum states having levels of map-information as coefficients of the states, grid qubit, in which geometric shapes are encoded in quantum states, quantum lattice, wherein color pixels are stored in quantum systems qubit by qubit, flexible representation of quantum image (FRQI), wherein the images are normalized states that capture the essential information about every point in an image, and R, G, B channels for map information.

3.1.1.3. To the quantum-map image in 2.1.1.2, map the syntrophic methane degradation processes subsystems of quantum circuitry along with colour-scales to describe the enthalpies and Gibbs energies of formation.

3.1.1.4. in the conversion of standard Gibbs free energy equations into their corresponding wavefunction model.

3.1.2. Virus trajectories 3.1.2.1. Obtain the G-quadruplexes for the virus species identified for the species in 1.2.2.1 and 1.2.2.4.1. These are highly conserved and also involved in the arrival of virus mutations.

3.1.2.2. For the Hilbert-space images of 2.1.1.2, apply the predicted virus-species G4 as a wavefunction to represent trajectory behavior and their timing using the following equations: represented by moving nodes in a "nodal point-X-point complex" (NPXPC) mechanism by the following expressions[11] as feasibly as possible where the images are near-term and not real-time:

$$m_i \frac{dx_i}{dt} = \frac{\hbar}{G}\left(\frac{\partial \Psi_I}{\partial x_i}\Psi_R - \frac{\partial \Psi_R}{\partial x_i}\Psi_I\right), i = 1, 2, \dots , \quad (1)$$

Where,
$\Psi = \Psi_R + i\Psi_I$ is a wavefunction guided by the time-dependent Schroedinger equation $\hat{H}\Psi = i\hbar \partial \Psi / \partial t$ and $G = \Psi_R{}^2 + \Psi_I{}^2$ (refer to Bohm Mechanics references cited in Tzemos and Contopoulos (2020)).

The time-dependent state $$\hat{\alpha}|\alpha(t) = A(t)|\alpha(t) > \quad (2)$$

Where,
$\hat{\alpha}$:=annihilation operator
$A(t)=|A(t)|\exp(i\phi(t))$:=the complex eigenvalue
The wavefunction corresponds to the state$|\alpha(t)>$ in the position representation given by $$Y(x, t) = \quad (3)$$

$$\left(\frac{m\omega}{\pi\hbar}\right)^{\frac{1}{4}}\exp\left[-\frac{m\omega}{\pi\hbar}\left(x - \sqrt{\frac{2\hbar}{m\omega}}\mathcal{R}[A(t)]\right)^2 + i\left(\sqrt{\frac{2m\omega}{\hbar}}\mathcal{J}[A(t)]\times \square(t)\right)\right.$$

with $$\mathcal{R}[A(t)] = a_0\cos(\sigma - \omega t), \quad (5)$$

$$\mathcal{J}[A(t)] = a_0\sin(\sigma - \omega t)\xi(t) = \frac{1}{2}\left[a_0^2\sin(2(\omega t - \sigma)) - \omega t\right],$$

Where $\sigma=\phi(t)$ is the initial phase of the complex eigenvalue $A(t)$ and $a_0 \equiv |A(0)|$
Bohmian flow motion at each node, relative to position coordinates on the map, referred to here as (x, y) in representation of two non-interacting 1-dimension oscillators:

$$H = \frac{p_x^2}{2m_x} + \frac{p_y^2}{2m_y} + \frac{1}{2}m_x\omega_x^2x^2 + \frac{1}{2}m_y\omega_y^2y^2. \quad (6)$$

For which the state of the system is defined by corresponding wavefunctions of the form, in an example given by Tzemos and Contopoulos (2020):

$$\Psi(x, y, t) = c_1 Y_R(x, t)Y_L(y, t) + c_2 Y_L(x, t)Y_R(y, t), \quad (7)$$

where $$Y_R(i, t) \equiv Y(i, t; \omega = \omega_i, m = m_i, \sigma = \sigma_i), i = x, y \quad (8)$$

$$Y_L(i, t) \equiv Y(i, t; \omega = \omega_i, m = m_i, \sigma = \sigma_i + \pi), i = x, y.$$

And each $Y_R$ and $Y_L$ are the one-dimensional coherent states with center started to an arbitrary right and left from the center of the oscillation along x and y, on each map-image.

3.1.3. Repeat the process given by 1.1 for the prediction of a new future drought and/or environmental extreme event.

3.1.4. Virus mutations 3.1.4.1. Using the circuit that describes the environmental change as an input leading through the thermodynamics of new virus evolution, and into the output of a newly evolved virus species (state), report the overall system as enthalpies and Gibbs energies of formation in a circuit that can calculate the evidence of a new virus mutation based on the report of 3.1.4.2. Mutations are represented by variations in the virus codons. While they and their hosts will still remain negative in the Gibbs thermodynamic energy equation and in all standard molar entropies, the number of distinguishable configurations of the codons for a virus with m matches can be predicted by $$\ln\Omega(E) = \ln P(E) + \frac{\sum_{j=1}^{n_E} P_j(E)\ln D_j(E) - P_j(E)\ln P_j(E)}{P(E)}$$

With $$\ln D_j(E) - \sum_{i=1}^{w_j} n_{ij}[\ln\Omega_0(m = m_i)]$$

depending on the number of matches (m), length of the virus and target genome length, the size of the alphabet, and the number of codons used (and not used) in the target. (Refer to Jones et al, (2015)[12]

3.1.4.3. The uncertainty in the standard Gibbs energy of formation of live matter, $\delta(\Delta_f G^0(bio)$, in Popovic (2019)[13]

$$\delta\left(\Delta_f G^0(bio)\right) = \delta\left(\Delta_f H^0(bio)\right) + T \cdot \delta\left(S_m^0(bio)\right)$$

$$P_{mut}(\Delta m = -1) = \omega\frac{m}{100}\left(\frac{1}{1 + e^{-(m-10)/2}}\right)$$

$$P_{mut}(\Delta m = +1) = \frac{\omega}{235.45}\left(e^{4.709(1-m/50)} - 1\right)$$

$$P_{mut}(\Delta m = 0) = 1 - P_{mut}(\Delta m = +1) - P_{mut}(\Delta m = -1)$$

3.1.4.3.1. The representation of new virus mutations is found for all temperatures and immunities in one stable (non-trivial, non-zero) eigenstate. At very low temperature, the virus must closely match the target genome. As temperature is rises, the mean number of matches of the quasistate decreases, eventually excluding a full match while at low immune amplitude, as T increases, the mean of the distributions moves smoothly from high match to low match (m-14.5) and at higher immune amplitude, the quasistates distribution jumps from higher to lower m 3.2. Finally, from the velocities per volume of predicted newly evolving virions determined according to Bohmian mechanical equations of trajectories which predicts the adjustments to be made in the corresponding distribution of pharmaceutical ingredients such as those given by this application that specifically target and disrupt the cellular respiratory and metabolic machinery of the virus archaeal-proteobacteria (VAB) in the human host's oral microbiome and in order to expose the host's saliva to components of the broken organisms in the presence of nZVI in order to deliver critical information will activate specific T- and B-cells for a pre-immunity immediately and for the duration of chewing such gum-product; the velocities to a pharmaceutical algorithm for the ingredients based on the following quantum circuit to calculate the map of the outbreaks, accordingly in each location shown by the intersection of trajectories with human populations:

3.2.1. Using the species found in 1.2.2.1 and 1.2.2.4.1 determine the expectation value of the energy of a viral state with N total viruses with a maximum of 100% matches in the environment at a given $E=N\Sigma_{n=0}^T(r-m)P(r)$, where r represents the genetic codon length 3.2.2. Where the trajectory is represented by the scars of the Lissajous trajectory followed by phase-related spread over new areas with a subsequent and repeated return, that represents an outbreak event.

Summary of Dependent Input-Variables

1. Human non-swallow food Ingredients
   Biodegradable or non-biodegradable chewing gum
   Pharmaceutical-grade nanoscale zero-valent iron (nZVI) particle
   *Komagataella phaffii* (*K. phaffii*) yeast
   Phytohemagglutinin (PHA)
Summary of Independent Variables
   Human or DigitalTime
   Map parameters (Latitude, Longitude)
   Population parameters
   Drought variables
   Temperature
   Acid variables
   Tertiary source Contour information variables
   Temperature annual gradient
   Temperature daily gradient
   Temperature 4-day gradient
   Rainfall event parameters
   Storm events parameters
   Inter-storm duration
   Moisture persistence
   Wind gust events
   Aquatic pressure
   Aquatic Temperature
   Aquatic Temperature annual gradient
   Aquatic daily temperature gradient
   Aquatic Temperature 4-day gradient
   Per monitor-regional Coverage area
   Population_of_zipcode/coordinates
   Industry variables: Agricultural, Chemical, Energy methanogenic sources
   Shared Habitat variables: Wildlife and Vegetation Species

ADDITIONAL NOTES

Archaeal methanogens are exceptionally high in pork and cattle, and especially salted products. The conversion of methane provides the basis for increased multiplication of archaea and their symbionts, which include *Prevotella, Streptococcus* and other bacteria that are found in the gut and hindgut of healthy livestock, including chicken. However, when ingested by humans, archaea render severe disease including the symptoms of disorders in the gut that lead to virus infection. Correlations between the volume of methanogens orally and in the intestine reveal that human recovery is faster when median durations of SARS-CoV-2 virus RNA persistence is significantly longer and higher in faecal swabs than in oropharyngeal swabs or in respiratory signals. Recent research also describes that the methanogenic archaea possess a cofactor F0/F420 molecule which is essential for methane biosynthesis (Glas et al. 2009). The severe virus-related outbreaks disease of pandemics have occurred directly within archaea-syntropic anaerobic bacterial partnerships of the SARS-CoV-2 pandemic, following the worst drought in Europe- and it infects TMPRSS2 and dACE-2 receptors at the highest levels in the small intestine, in the same location as the highest levels of methane by archaea. Methane gas accumulation is not only painful but, during virus-related infection, methane causes intestinal wall perforation and burn scars observed in fatal victims of virus-related disease.

On average, modern human's breath can carry more than 300 ppb of methanol3[14] and higher during virus-multiplication following epidemic or pandemic infection and disease outbreak. This is because the methanol products of methanogenesis enables accelerated virus multiplication, resulting in a higher probability of disease risk to the human within the downstream digestive tract where infectivity sites are the highest in their acidic extremophilic and anaerobic bacterial environments. In humans, methane production is found highest for strains of the genus *Clostridium*, intermediate with anaerobic cocci and least with *Bacteroides* species. Very few strains produce methane in healthy humans although small amounts have been detected with *B. thetaiotaomicron, C. perfringens* and *C. histolyticum*, normally only in gut and hindgut of ruminal animals whose tissue is fed to humans in mass-food production industries. Spread It has been established in the research that asymptomatic, pre-symptomatic and symptomatic infected individuals who come in close contact with healthy persons are apt to spread a pandemic or epidemic disease via breath, cough and even singing. It is described that infected droplets and aerosols from human breath is sufficient to be the cause of such spread. For this reason non-pharmaceutical intervention such as oronasal coverings (masks) have been suggested on the basis of the droplets. This is because the oral cavity is shared with the nasal cavity.

However, masks which are varied in fabric, re-use and design have no consistent scientific validity in preventing spread of viruses, and are reported with an effectiveness against pandemic-spread prevention around 50%, including in crowded areas. In addition, environmental extremes that result in nutrient-deprivation triggers General Stress Response (GSR) that includes high levels of bacteria motility, equivalent to escape responses in flight-or-flight stress conditions. Motility is altered by changes in the environment according to the GSR-activating phosphorelay, PhR-NepR/Nep2R gene expression of the stressed-bacteria globally. This is required for long-term residence in a mammalian host[15]. This includes the protobacteria hosted in humans described earlier.

Motility includes mechanical, vibromotor flagellar, chemotactic, magnetotactic and other energy-sensing results that enable the bacteria to conduct what is part of global pursuit of better nutrient-rich alternative habitats for growth. SARS-CoV-2 transmission can occur by activities involving toilet spray which delivers much higher virus replication particles and volume of finer moisture droplets, far more than from human breath. The GSR response activates adhesion and other spread mechanisms in bacteria. And yet, no indoor toilet covers were proposed by health officials simultaneous to outdoor masks.

Methane gas, as well as its byproducts ethylene and ethane upon breakdown by the methylotrophic pathway is a skin permeable gas including through masks which are porous enough for the transmission of virion particles. Methanogenic archaea include: *Methanobrevibacter oralis, Methanobrevibacter smithii,* and *Methanobrevibacter massiliens* in the oral cavity *plus, M. smithii, Methanosphaera stadtmanae, methanomassiliicoccus luminiyensis, Methanobrevibacter arboriphilicus, M. oralis, Ca. methanomethylophilus alvus, Ca. methanomassiliicoccus* in the gastrointestinal tract. Without archaea present, viruses do not graze in the human oral cavity and do not spread to the gastrointestinal.

Methanogens depend on the byproducts of anaerobic gut bacteria metabolism, such as acetate and hydrogen produced by anaerobic gut bacteria that are usually only found in cattle, swine, and fowl. (See FIG. 3.0.) These bacteria are also members of the phylum of Proteobacteria, whose members include significant oligotrophs and magnetotactic bacteria, for extreme-climate conditions and in the synchronisation properties of global spread. Without archaea present, indeed methane production from human bodies also drops. The relationship between disease, including cancer, and methane is therefore cut by the presence of the chewing gum and this may provide worthwhile advantages to delay immunocompromise risks and epidemic control. There are many more types of archaea, in addition to the ones in humans: including in food products where extremophiles and halophiles in high-salt meat products and a few types of fish, are found and need restriction following climate-extreme drought events. Each of them share the methane environmental and oral/gut pathway contamination. Unfortunately, 99% of all bacteria and viruses cannot be discovered or grown in a laboratory environment for database-recording. Specific extreme climate-change events are currently not precisely predictable by current machine-learning algorithms, either-including those which are based on historical data assembled in artificial intelligence (AI) simulations. Much of this has to do with the realistic challenges of data-collection some of which is solved by image analysis; plus, there are vital diurnal variations in growth and infectious genetic exchange that are not acknowledged by digital species evolution forecasts to-date. This means that currently there are no infectivity maps either, nor forecasts of new virus evolution following from climate change in habitats monitored by satellites and ground-level tertiary sources.

At the time of writing, the relationship between public health disease outbreak forecasting has not represent real-time integration to any available environmental methane monitoring resources (such as Sentinel 5 and Sciamachy geo-environmental methane-predicting satellites); nor does the public health agency of nations include groundwater and soil sampling for prediction of zoonotic disease post-extreme event.

Variable dependent and independent parameters are noted in this disclosure, all of which may be replaced with suitable equivalents to derive the thermodynamic relationships of new virus species to the GSR-activated bacteria that are the basis of virus-targets and their related pandemic and epidemic infectious spread phenomena in humans who are non-nomadic for a given habitat/site. The derivation is needed in order to prescribe appropriate modifications to the ratios of pharmaceutical ingredients in the chewing gum component of this disclosure.

The algorithm to predict a forecast is therefore constructed chiefly to adjust the ingredients to prevent infectivity and host-visibility to spread-encounter. The variations are described according to scientific opportunities A, C, G and U/T in a redundant genetic code with number of matches and lengths of genomes to the probability of successful immunity bypass according to ecological principles of ensuring nutrient recycling. The predictions include acknowledgement of virus' role in biodiversity preservation which does not represent the survival of only the fittest but rather, the sustainability of resources for- and by the maximization of the widest balance possible in ongoing species diversification (evolution).

No part of the quantum algorithm is required to be distributed with the chewing gum. The algorithm merely predicts the geophylogeny of species of viruses and in turn, this can be used to prepare pharmaceutical ingredients on behalf of disrupting the virus-archaeal-bacterial syntrophic relationship, accordingly.

The product primarily robs from methane resources of the archaeal-proteobacteria methyl respiration pathway and methylotrophic pathway in the oral cavity (FIG. 3.0). Secondarily, it stimulates immediate immunological (antibody) response in its bolus upon mastication with salivation-related aqueous fluid mix, as described below:

The Human Oral Microbiome Database (HOMD)[16], (www.homd.org) (HOMD) includes 619 taxa in 13 phyla, as follows: Actinobacteria, Bacteroidetes, Chlamydiae, Chloroflexi, Euryarchaeota, Firmicutes, Fusobacteria, Proteobacteria, Spirochaetes, SR1, Synergistetes, Tenericutes, and TM7 found in teeth, gingival sulcus, attached gingiva, tongue, cheek, lip, hard palate, and soft palate, and the distinct microbial habitats that are contiguous with the oral cavity including, tonsils, pharynx, esophagus, Eustachian tube, middle ear, trachea, lungs, nasal passages, and sinuses.

*Methanobrevibacter* species are archaea that produce $CH_4$ from $H_2$ and $CO_2$, and other products of correlated syntrophic bacterial fermentation of dietary fibers[17].

Using the degradation of glucose from polysaccharides complex sugars, endergonic syntrophic species of the human oral microbiome archaea and bacteria of alcohols and fatty acids degrade glucose into acetate and $H_2$ which thereby enables $H_2$-consuming methanogenesis during food consumption. And so, acetate and $H_2$ (alternatively format) plus $CO_2$ serve as substrates for methanogens[18].

Less than half of the available Gibbs free energy content of glucose is available for the syntrophic degradation of the alcohols and fatty acids to $CH_4$ and $CO_2$ that can be released to the ambient environment through breath or even skin. Such energy is efficiently shared among the syntrophs and the methanogens in the human oral cavity leading to their growth and survival, including with infectious outcomes to the human host. In Erdrich et al (2021)[19], human mean total gas concentrations pre- and post-mouthwash can exceed approximately 221.0 ppm and 152.1 ppm (p<0.0001) for hydrogen, and 368.9 ppm and 249.8 ppm (p<0.0001) for methane. The goal of this disclosure product is to sufficiently disrupt both the methanogenic percentage of energy available for the multiplication and also to prevent spread by disrupting the mechanical motility and adhesion of archaea and protobacteria in spread, and in the mechanisms in which they attract subsequent virus infectivity in the human oral niche.

It is done via the following methods:

a. *Komagataella pfaffi* in any modified form for chewing gum integration, where such yeast is derived from oak tree or other source that becomes active after saliva-aqueous exposure and fully activated to capture the methane produced by the methanogens adhering any-where in the mouth cavity such as on teeth; alternative methanol-assimilating yeasts may also be used; the alcohol oxidase and other enzymes required for the metabolism of methanol, and the peroxisomes in which the enzymes are formed fill much of the interior of the cell of *K. pfaffi* (de Koning and Harder 1992; Veenhuis et al. 1983 in[20]). This unique property has been utilized for expression of foreign proteins through linkage of the gene of interest to the promoter for the alcohol oxidase gene (Cregg et al. 1993).

b. Phytohemagglutinin (PHA) which is a lectin extract from red kidney bean (*Phaseolus vulgaris*) skin or other source by standard chromatographic techniques, consists of only L-type subunits (isolectin L4, "leuko-agglutinin") (see Sigma Aldrich[21], is an N-acetylgalactosamine/galactose sugar-specific lectin of which PHA consists of five isolectins (L4E0, L3E1, L2E2, L1E3, L0E4) each being a tetramer held together by noncovalent forces; it is described as leukocyte reactive, having a high affinity for lymphocyte surface receptors, but little for those of erythrocytes, and are responsible for the mitogenic properties of the isolectins such as high-efficiency induction of—and in the functional stimulation of human T-lymphocytes and for peripheral blood mononuclear cells (PBMC) stimulation, including stimulation of cell division and metabolic activity. Only 1 to 5 μg/ml is needed for the stimulation of human peripheral blood lymphocytes, distributed in a set of chewing-gum product ingredients consumed per day or week, as required, stored at −15 to −25° C. until use.

c. Nanoscale zero-valent iron particle (NZVIs) smaller than 50 nm up to 10,000 ppm for 48 hours which effectively degrade the iron component of proteobacteria involved in the $H_2$-generation and reduces the mass flux within the oxygen-containing oral air-aqueous mixture. The reaction of nZVI with 02 in human breath can produce reactive oxygen species (ROS) either on the particle surface within the chewing gum, which is not swallowed, and while the ferric-byproducts of the syntrophic relationship of the proteobacteria is corroded (as well as any other potential organic or inorganic contaminants) in less than 2 hours including after the chewing gum has been disposed. Nontoxic, they oxidize Fe0 to Fe2+ and then to Fe3+, leads to the production of reactive oxygen species (ROS), resulting in the generation of hydroxyl radicals (OH—) from superoxide (O2-) and hydrogen peroxide ($H_2O_2$) in microbial cells[22]. These radicals cause bacterial cell membrane damage, leading to the outflow of intracellular contents and, ultimately, cell death such that the fragments are trapped by the chewing gum mass. The reaction of nZVI with O2 can produce reactive oxygen species (ROS) either on the particle surface within the chewing gum which is not swallowed. According to Keenen et al (2008),[23] the result of these reactions includes the generation of trace amounts of hydrogen peroxide ($H_2O_2$) during the oxygenation of Fe(0), wherein $H_2O_2$ subsequently reacts with Fe(II) to produce hydroxyl radicals (HO·) and/or Fe(IV)O2+ species via the Fenton reaction[24-27]. While the formation of these byproducts is a concern if swallowed, they provide substantial decontamination of syntrophic pathogenic species from the environment that invade the human oral cavity.

Any state-of-the-art chewing gum may be used to host the *K. pfaffi*, nZVI and PHA pharmaceutical ingredients.

The chewing gum has been described primarily in terms of its ability to host pharmaceutical ingredients in combinations that are both bactericidal and methanogen-removing in order to disrupt the syntrophic domain in infectious spread from human oronasal breath-saliva mixture. One of the outcomes of chewing the gum includes immunological salivary-driven T-cell and B-cell activation. These cells intrinsically respond to the NSVI particles and any virion particles trapped on their surface, as part of the interaction with salivary proteins during mastication. The use of the quantum circuit algorithm creates an opportunity to predict changes to the ratio of ingredients mixed in the gum according to the genomic structure of a future virus-disease outbreak. The circuit will be described in the next section but, for now, these ratios are based on user-specific frequency of use and the required user-specific frequency of use. The required user-specific frequency of use combines $\Delta_Q$, the duration of chewing. For example, the ideal duration is two hours but, a new chewing gum may be replaced after one hour. The minimum is one hour.

The TOD is also relevant and should include human-immune regulation transition periods based on the period in which the solar-dusk to brightest-daytime transition matches with genetic transition from immunity-protection state to immunity-repair periods. Typically, this is from awake-state to sleep-state. And so, the ideal time for chewing gum is at dusk, as well as during shared environments with other humans. This achieves pre-immunity protection as well as decreasing non-infectious virus-multiplication hosting in post-immune stages. The limiting ingredient may also be varied.

Methylotrophic yeasts such as *Komagataella phaffii* are considered to use alcohol oxidases to assimilate methanol, different to bacteria which employ alcohol dehydrogenases on behalf of growth. Yeast cultures stimulate acetogens to outcompete or co-metabolize hydrogen with methanogens during fermentation[28]. The yeast *Komagataella phaffii* carries two genes coding for alcohol oxidase, AOX1 and AOX2. In general methanotrophs, bacteria that use methane as an energy source, convert methane into methanol. Methanol metabolism takes place in assimilatory and dissimilatory pathways of the ingredient *K. phaffii* via the peroxisome enzyme (see: Rußmayer et al. 2015; and Yurimoto, Kato and Sakai 2005; van der Klei et al. 2006; Vanz et al. 2012; Rußmayer et al. 2015 in Zavec et al, 2021[29]. However, the conversion of methanol does not need to be simultaneous with new cellular growth of this yeast[29]. The rate of methanol uptake starts immediately and is as high as 97%, at over 10 g/L consumption by the *K. phaffii*, in the research of its genetic methanol-conversion relationships[29].

As well, in this disclosure, non-yeast variations can be used as a substitute to reduce methane such as sunflower oil and ionophores where such ingredients may be feasibly mixed into the chewing gum.

If the limiting ingredient is NVZI, then he suggested gum assembly is based on $\Delta_{Q_{NVZI}}=1$ hour for TOD>17 (based on at least 1 NVZI particle 50 nm up to 10,000 ppm for 48 hours) with the proportion of the PHA ingredients ranging between 1 to 5 μg/ml.

During an outbreak the mixture of the ingredients is prepared in proportions of each ingredient according to the feedback of the environmental monitors and QTC, for emergent and existing species evolution. (see FIG. 1.0.) Mastication of the ingredients prevents archaeal survival by removing archaea including those that may be involved in repair of DNA that has been exposed to UV-radiation treatment in antigenic antivirals such as in clinics. Mastication can also change the methane chirality which reduces its bioavailability to the mass flux.

Mastication of the gum also traps virion particles that are otherwise present in logarithmic-higher number-densities than the bacteria on which they graze within the oral cavity.

Chewing the gum activates increased salivation. Saliva is largely aqueous. Proteins and polypeptides produced by archaeal-virus microorganisms accelerate methane-hydrate formation. The mechanical pressure of mastication thereby captures the archaeal microbe mass involved in this process of hydration and leads to the reduction of methanogenesis 1 in the gum-user. The importance of this methanogenic alteration is its key characteristic of disabling the rate and speed of disease infectivity by virus and thereby providing the virtual infrastructure that prevents spread. Archaea colonizing the human microbiota include these methanogens, traditionally characterised by their broad-spectrum resistance to antimicrobial agents, and for their growth which depends on hydrogen to reduce methanol to methane, plus on carbon dioxide, biotin and other compounds. Human breath can carry more than 300 ppb methanol, as stated earlier, and higher during virus-multiplication following epidemic or pandemic infection and disease outbreak. This is because the methanol products of methanogenesis enables accelerated bacterial-virus multiplication. Moreover, in humans, methane production is found highest for strains of the genus *Clostridium*, intermediate with anaerobic cocci and least with *Bacteroides* species. Very few strains produce methane in healthy humans although small amounts have been detected with *B. thetaiotaomicron, C. perfringens* and *C. histolyticum*, normally only in gut and hindgut of ruminal animals whose tissue is fed to humans in mass-food production industries. Thus, the chewing of the gum results in a lower probability of disease risk to the human within the downstream digestive tract where infectivity sites are at their highest percentage and vulnerable to their acidic extremophilic and anaerobic bacterial events.

The use of the product includes post-meals regularity.

The product changes the infectivity immediately within the destruction of the syntrophic methane basis, per human user.

It reduces spread-rate potential in a crowd of users, eliminating for example the hydrogenotrophic-methanogens which are temperature sensitive (leading to seasonality of outbreaks) and which induces anaerobic species of bacteria that are suspected of gaining additional antibiotic resistance from their archaeal symbionts (Clause 10). In this way, the product represents a breath-and-saliva type of sanitizer.

Description of How the Independent Input-Variable Work:

Upcoming virus species will need their host's cellular machinery to replicate. The steps include cellular penetration such as via membrane fusion, endocytosis or genetic injection. RNA mutation rates are high due to the nature of a biodiversity-survival urgency in the presence of drought. This ensures high numbers of progeny quickly, within days, such as via cell budding, apoptosis or exocytosis which results in host death. The mutations enable the immune system to be evaded and to also overcome antiviral pharmaceutical resistance in the host such as from traditional vaccines. Most importantly, this process means that a virus genetically must be complementary to the genetic receptors that it targets in the host cell. The use of the product developed by this disclosure's quantum circuit is ideal to ensure immunological response activation customized to a future virus outbreak that can be modeled by the algorithm months or even years before the virus outbreak occurs as long as a drought—or other climate-change extreme has been detected in any state-of-the art forecast for a given habitat with known dominant living species (terrestrial or aquatic).

To do so, we recognise that there are three underlying bases (A, C, G and U/T) in a redundant genetic code. Alternatively we may choose the G-quadruplex which is directly known to be involved in virus mutation in pathogenic disease according to available tertiary databases. The number of matches between host and target sequences is a maximum of joint probability distributions in the quantum circuit output. This correlates to what is referred to as viral infective fitness in the research[12]. Determination of the matches is done according to the circuit, with input corresponding to general stress response (GSR) activation. During GSR, PhyR phosphorylation at the intra-cellular level results in a large conformational change which lowers the energetic barrier to NepR-binding site and rendering an open state conformation to RNA transcription, both revealing the NepR-binding site on the PhyR SL domain (Campagne et al., 2012, Herrou et al., 2012) in Leubke et al (2018)[3] and enabling changes in gene-expressing stress related changes such as motility. During GSR, when bacteria experience multiple stresses under environmental conditions that include pH, temperature but most importantly, the shortage of nutrients during drought, motility can be represented as a system of spread that is activated because of these climate-change parameters. The fact that all bacteria share the same core regulators of GSR, means that all will express stress-dependent alternative sigma factors that all compete with GSR-sigma factors for binding to the RNA polymerase to redirect transcription towards stress response genes and their results in favour of organism survival. This means that all bacteria involved in traveling or spreading to new locations, which is the basis of spread. This includes, for example, SigmaS in beta-, gamma- and deltaproteobacteria; SigmaB in some Gram-positive bacteria; and, an ECF (extracytoplasmic function) sigma factor in alphaproteobacteria GSR. Regardless of how the response starts, such as with the direct or indirect activation of PhyR or its orthologues by signal-integrating histidine kinases or other members of the same the HWE/HisKA2 family[3], in the RNA polymerase redirects transcription which initiates and sustains the GSR-activation by binding with EcfG, and is referred collectively as the GSR-activating Phosphorelay[3]). And so, in another variation, the model may represent phosphorylation directly within its extracellular functional sigma factor.[3]), anti-sigma factor (NepR) and/or alternative sigma factor (EcfG) in the additional pharmaceutical derivations of the disclosure's product-development.[3]).

In a further variation, this disclosure may be used in an assembly to annotate real-world digital evacuation maps or pandemic-prevention and reporting tools in any geographic information system.

This means that the chewing gum whose use is intended to sanitize and stop spread via airborne infectious saliva-hosting pathogenic species in human breath, based on ingredients that are varied in their proportions according to the joint probability distribution of greatest density at the receiving source of the generated output from the quantum circuit algorithm. This receiving source, by its mathematical nature, has shared phase and frequency properties that describe the genomic structure of the excitatory source, i.e., the species source for which the viral genome necessarily emulates in matching components of its own genetic morphology for replication with the host's cellular machinery. In so doing, the use of the forecasted virus genome morphology in the quantum circuit execution can also be used to calculate related viable virus mutations and then, to plan suitable pharmaceutical readiness for a maximum of these species along with other interventions including population-evacuation. When the chewing gum is used on a regular basis, for multiple specific virus outbreaks, it describes a socially-enabled virtual infrastructure in public health.

Method of predicting virus species and spread in order to derive chewing-gum product's pharmaceutical ingredients and target human populations:

Recall, the disclosure refers to the thermodynamic temperature of a system to describe the genomic relationship between the new virus-species and the non-nomadic human that happens to be resident in a drought- or nutrient-challenged habitat. This human becomes the target-host if corresponding GSR-species of the dominant species microbiome are mutually shared.

Temperature of the system means that the viruses do not stay in one equilibrium microstate but sample all accessible states with a probability based on the Boltzman distribution.

The total number of cells, size of the generic genomic alphabet, length of viruses and target host genomes are the system constraints.

The expectation value of the energy of a viral state with N total viruses in the environment at a given temperature and immunity is given by:

$$E = N \sum_{m=0}^{50} (50 - m)P(m) \tag{0}$$

Where m:=the number of matches

E increases monotonically with temperature and equals zero all along the temperature axis for T=0 corresponding to full immunity.

Provided the cells and environment are both in contact, all possible viruses are in thermal and chemical equilibrium, then the particle number must have an associated chemical potential for which the use of the Schroedinger time-dependent equation to represent the new species is appropriate, below. Thus, the accessible states at the energy E corresponding to the thermodynamic T is $$\frac{1}{k_b T} = \beta = \frac{\partial \ln \Omega(E)}{\partial E}$$

where $\Omega(E)$ is the accessible states at energy E, for an entire cohort of N viruses and the viral state at equilibrium has as its properties, $f(T_{effective}, \text{Immune strength})$. This implies that the average energy is a function of the number of viruses and the probability distribution of the number of genetic matches (and mismatches) between the viruses and the available targets (humans). The thermodynamic temperature is the sum of all systems within the virus trajectory that have a state that can be described by the probability distribution function, represented in our Schroedinger equation for the Bohmian flow, below, in each of the accessible states of energy belonging to their mutations, which in turn, within the energy resources contributed by the available elements (nucleic acids) of the virus genomic structure. One may define the accessible states along a temperature scale set by the entropy for the genetic properties of the virus and host-target pair. In this way, each type of virus with a protein receptor of different length or different mutation-'degeneracy" or different host/target receptors can be compared by reviewing the changes in entropy and the thermodynamic energy. In the design of a pharmaceutical metric, this temperature can be used to determine the set of ingredients that effectively cause the change in entropy that is the equal and opposite of the virion infection. This is equal to the slope of the line $k_B T_{thermodynamics}$ from a plot of ln $\Omega(E)$ vs E.

Thermodynamics requires conservation of energy and so, by definition, the system is described to enter zero energy (ground state) at Temp T equal zero.

The quantum system of entanglement (QE) is used as the physical property representing the quantum mobilization of virion particles, used in a prospective computation such as a quantum information circuit. It governs the quantum probabilities of subsystems, describing the movement of spread, which represent a geometric lattice structure on the plane (described here as on the plane (x, y) (or any other reference grid) for the plane of virus-particle interaction, including from initial emergence into multiplication-supporting environments at any time t.

The trajectories of viral genome evolution from a source-habitat with dominant species into a density of spread measurement for a new outbreak can be ideally represented by the model of moving nodes in a Bohmian system of trajectories. This trajectory system includes Lissajous-like patterns. The system is represented by moving nodes in a "nodal point-X-point complex" (NPXPC) mechanism by the following expressions[11]:

$$m_i \frac{dx_i}{dt} = \frac{\hbar}{G}\left(\frac{\partial \Psi_I}{\partial x_i}\Psi_R - \frac{\partial \Psi_R}{\partial x_i}\Psi_I\right), i = 1, 2, \dots ,$$ (1)

Where, $\Psi = \Psi_R + i\Psi_I$ is a wavefunction guided by the time-dependent Schroedinger equation $\hat{H}\Psi = i\hbar \partial \Psi / \partial t$ and $G = \Psi_R{}^2 + \Psi_I{}^2$ (refer to Bohm Mechanics references cited in Tzemos and Contopoulos (2020)). The time-dependent state $$\hat{\alpha}|\alpha(t) = A(t)|\alpha(t) >$$ (2)

Where, $\hat{\alpha}$:=annihilation operator $A(t) = |A(t)|\exp(i\phi(t))$:=the complex eigenvalue The wavefunction Y corresponds to the state$|\alpha(t)>$ in the position representation given by $Y(x, t) =$ (3)

$$\left(\frac{m\omega}{\pi\hbar}\right)^{\frac{1}{4}} \exp\left[-\frac{m\omega}{\pi\hbar}\left(x - \sqrt{\frac{2\hbar}{m\omega}}\mathcal{R}[A(t)]\right)^2 + i\left(\sqrt{\frac{2m\omega}{\hbar}}\mathcal{J}[A(t)]x + \square(t)\right)\right.$$

with $$\mathfrak{R}[A(t)] = a_0 \cos(\sigma - \omega t), \mathcal{J}[A(t)] = a_0 \sin(\sigma - \omega t)$$ (4)

$$\varepsilon(t) = \frac{1}{2}\left[a_0^2 \sin(2(\omega t - \sigma)) - \omega t\right].$$ (5)

Where $\sigma = \phi(t)$ is the initial phase of the complex eigenvalue A(t) and $\alpha_0 \equiv |A(0)|$ Bohmian flow motion at each node, relative to position coordinates, such as (x, y) in representation of two non-interacting 1-dimension oscillators:

$$H = \frac{p_x^2}{2m_x} + \frac{p_y^2}{2m_y} + \frac{1}{2}m_x\omega_x^2 x^2 + \frac{1}{2}\omega_y^2 y^2.$$ (6)

For which the state of the system is defined by corresponding wavefunctions of the form, in an example given by Tzemos and Contopoulos (2020):

$$\Psi(x, y, t) = c_1 Y_R(x, t)Y_L(y, t) + c_2 Y_L(x, t)Y_R(y, t),$$ (7)

where $$Y_R(i, t) \equiv Y(i, t; \omega = \omega_i, m = m_i, \sigma = \sigma_i), i = x, y$$ (8)

$$Y_L(i, t) \equiv Y(i, t; \omega = \omega_i, m = m_i, \sigma = \sigma_i + \pi), i = x, y.$$

And each $Y_R$ and $Y_L$ are the one-dimensional coherent states with center started to an arbitrary right and left from the center of the oscillation along x and v.

In the disclosure, the states may be chosen to represent real-map orientation for the reference to Clause 3, relative to a target human population.

1. Trajectory points are initially distributed in sets, such as $S_1$, $S_2$, . . . $S_n$ for initial representation of virion particles without violating Born's rule. Each set of parameters which define the different environmental conditions of new diseases must result in the same limiting distribution of trajectory points, which means towards the same virus genomic assembly and for the same target, the measurement of entanglement produces ergodicity for each of the individual Bohmian trajectories as t→∞(refer to Clause 4)

2. The Bohmian Trajectory (BT) is a non-symmetrical nonlinear trajectory of motion and the existence of chaos is necessary for the convergence of the trajectory probability density to Born's Rule. By exploring this chaos in the presence of QE. the essential characteristics of the BT in an entangled qubit system model includes physical parameters describing the behavior of spread as a quantum harmonic oscillator where $$\frac{w_x}{w_y}$$

determines if the chaotic motion at each node is irrational, periodic or integrable $$\left(\frac{w_x}{w_y} = 1\right)$$

for an infinite number of nodal points of the wavefunction, forming a time-varying lattice structure.

3. The moving nodal lattice structure is a geometric structure representing the virion related Bohmian Flow, a moving nodal point-x-point complex (NPXPC) as described in [11] for experimental scientific exploration and/or derived as a map with coordinates that are meaningful for greater distribution analysis related to the use of the trajectories in the chewing gum (or other) pharmaceutical product distribution end-points.

4. Chaos affects the manner in which the Bohmian Trajectories cover/saturate the configuration state which is considered the infective space. In Clause 2, the use of Born's Rule at any time t of the spread trajectory is $P=|\Psi|^2$.

5. The entanglement depends on values of the constants $c_1$ and $c_2$ which are used to control the amount of entanglement, such as $$c_2 \epsilon \left[0, \frac{\sqrt{2}}{2}\right] \text{ for } c_1^2 + c_2^2 = 1$$

and where $c_2=0$ represents the product state and the $$c_2 = \frac{\sqrt{2}}{2}$$

represents the maximum entangled state.

6. Quantum entanglement in this model is conserved by absence of interacting terms in the Hamiltonian.

7. Positions of the nodal points of the wavefunction (7) are solutions of the equation $\Re\,\Psi = \Im\,\Psi = 0$ and evolve in time based on:

$$x_{nod} = \frac{\sqrt{2}\left(k\pi \cos(\omega_y t) + \sin(\omega_y t) \ln\left(\left|\frac{c_1}{c_2}\right|\right)\right)}{4\sqrt{\omega_I}\,a_0\,\sin(\omega_{xy}t)} \tag{9}$$

$$y_{nod} = \frac{\sqrt{2}\left(k\pi \cos(\omega_x t) + \sin(\omega_x t) \ln\left(\left|\frac{c_1}{c_2}\right|\right)\right)}{4\sqrt{\omega_y}\,a_0\,\sin(\omega_{xy}t)} \tag{10}$$

With $k \in Z, k=$even, for $c_1 c_1 < 0$ and $k=$odd, for $c_1 c_1 \geq 0$

And $\omega_{xy} \equiv \omega_x - \omega_y$

8. Distance between given nodal points such as on a map-meaningful coordinate grid, and labeled with k-integer values (e.g., $k_1$ and $k_2$) is $|k_1 - k_{i=1}|$ at every given time t.

9. Entanglement decreases as the central empty regions enlarge because the increased density in one given area is simultaneous with the decreased velocity of the k-nodes in the area. In other words, the increased entanglement confines the "slow part" of the nodal trajectories when they are closer to the source (origin) and that there is expected higher-speeds closer to the locations of infection. However, the nodal points with higher velocities do not affect the Bohmian Trajectories.

10. The bohemian trajectories of virion particle spread approach a Lissajous behaviour whose size is the same for all initial conditions. The chaotic behavior of the Bohmian trajectories are equal to lissajous curves even for very small values of $c_2$ for a significant portion of the model-time, and then the model behavior becomes chaotic again due to close approach with a nodal point and its associated x-coordinate. As the value of $c_2$ decreases to $c_2=0.01$ from $$c_1 = c_2 = \frac{\sqrt{2}}{2},$$

the maximum density of nodal points are distributed in the same geometry but are found closer to the source-center.

11. As the nodal point passes an infinite number of times (oscillation dynamics) inside the wavefunction of the system (corresponding to the region of the configuration-space on which the value P is relatively high), there is a high probability of close interaction between the nodal points and the trajectories mutually. And so the nodal points form the structure of quantum flow corresponding to the nodal-point-X-point complex of the virus spread (virus NPXPC). This configuration space specifies the region for pharmacological investigation between the virus genome identification in Clause 4 and in order to identify precise user-readiness locations for the modified chewing gum described in Clause 2.

ADDITIONAL VARIATIONS OF THE DISCLOSURE

1. Real-world monitors or satellites detect the environmental signals given earlier as independent parameters, which are referred to in Clause 3. In a variation, the monitors can include locally-determined sigma factor-mediated transcriptional control by specific species by laboratory findings.

2. The independent parameters must indicate the record of drought, relative to pH, salinity and other factors that disable nutrient availability to bacterial species in general and which will trigger virus response related to their sustainability. Such records represent the biotic parameters and they affect motility from a nutrient-poor habitat to a nutrient-rich alternative, according to scientifically visible GSR responses at the cellular level. In another variation, other or existing models may be used to describe the receiver (REC) proteins (regulators) directly, including a description of the cellular physiological responses per species as a function of their species' phosphorylation state to a drought-threat or other environmental threat rather than as a function of a constant motility-readiness or based on multiple features of peri-escape and survival behaviours that are part of the infectious-probability of resulting disease spread. This may include, for example, existing research models which describe GSR based on two classic gene regulatory paradigms: a two-component signaling and an alternative sigma (a) factor regulation, in which the PhyR protein lies at the center of this pathway, comprising a C-terminal receiver (REC) domain and an N-terminal a-like domain (Francez-Charlot et al., 2009, Herrou et al., 2010) in Leubke et al (2018)[3].

3. In another variation, the quantum circuit may model PhyR/PhyT in gradients of behavior representing emerging stress-response gradients and lethal GSR overactivation prevention mechanisms of specific bacteria species.[3])

4. In another variation, the quantum circuit may be modified to represent a dual system of infectivity based on methane in humans and the environmental network, and/or a genomic network based on available scientific genetic repositories for genes that represent early warning of pre-outbreak GSR; this can include models of the sigma factor EcfG or its orthologues and which characterize the bacterial envelope modulation, signal transduction and stress protection to all bacteria during an emergent pandemic following drought.[3]). Such a circuit may be used to model the GSR-controlling sigma factor and EcfG of bacteria in a given habitat based on the best available scientific knowledge today and that will be found in the future in order to predict the associated proteins which encode directly for stress protection by bacteria whether these proteins are part of a drug-related product assembly invention or that may be caused by a potential harmful industrial discharge in their habitat; such proteins include the catalases, thioredoxin reductase, peroxiredoxin, NADH:flavin oxidoreductase and 2 DNA binding ferritin-like proteins, the set of which provide protection against salt and osmotic stress, and other environmental stress.[3]). And so, the quantum circuit described in this disclosure can be adapted to report GSR as a paradigm that which provides utility to identify genes that are regulated by EcfG and the negative GSR feedback regulator activation, including the importance of NepR2 as part of non-stress return of the species following the return and restoration of environmental health to a previous nutrient-threat location.

5. In one variation of the circuit design, the trajectory alignment may incorporate a circuit for modeling real-time weather intrusions, where speed is altered by precipitation, volcanic eruption, and geoclimatic or physical industrial intervention events that alter the trajectory distance with emergent knowledge.

6. In another variation, specific bacteria body lengths per second may be used for comparing speed and for calculating energy and expenditure based on different bacteria cell size; trajectories may be expressed as travel-run length relative to environmental diffusivity and gradient of travel such as for establishing and testing hypotheses on physical limits of spread and in order to determine specific chemotaxis periods in prescribing pharmaceutical anti-spread barrier devices separately from the chewing gum product described in this disclosure.

7. In another variation such as research where bacterial movement is already known or easily measured for absolute speed, constancy of Speed, turn-and-go gradient length, the specific size, receptor sensitivity and the extent to which any other motility of motion can be biased, may be used; this suggests considerable scope for additional product variation where bacterial mortality and chemotactic strategies are part of environmental health and ecological safety applications of the disclosure, including in settings where there may be steep complex and dynamic chemical gradients period, or where bacteria are treated so that they cannot move or where the number of departures from a model showing a uniform trajectory between outbreak points is not valid but that it should include variations such as additional run and tumble chemotaxis, helical klinotaxis, between nutrients versus poisons in the environment.

8. In another variation, the quantum circuit may be described in compartments relevant to specific motility, as given in scientific research standards for bacteria in bulk fluid, near-surface bulk fluid and near-surface constrained fluid. This may include applications to do with specific regions of the human oral cavity and shared air, to do with research about eating and hazards of certain high-risk food manufacturing.

9. Pharmaceutical measurement must highlight pH, salinity and temperature specifically for airborne and for saliva-based interaction for bacteria swimming parallel to the surface (Clause 6). The aspect ratio of the cell determines how much are cells motile and in what way, and for what size populations such as 10 to 100 million cells. In a technology-variation, it may be possible to include and measure the rotational drag coefficient, the average measurements being based on attachment of detecting-particles to the specific bacteria in order to obtain these motile-interaction rates, accordingly.

10. In another variation, electrochemical gradients of $H+$ or $Na+$ generated across the cytoplasmic membrane may be used to test and alter the design of the chewing gum product's effectiveness in stopping airborne bacterial motility during saliva-based exhalation. This includes designing the gum as though it were a true mechanical-molecular machine so to speak, that recycles bacteria-virus particles into electric chemical energy to clean and/or restore some useful properties of the gum during mastication. *Streptococcus* species are the $H+$ driven type, for example.

11. In another variation, the chewing gum may be used as sensors themselves in order to detect and report gradients in the environment as small as 10 micrometers with the bacteria that are trapped and such as where the disposed chewing gum is inserted into an analyser with other humans in local collection facilities or discretized biowaste pre-processing analyses or as part of a vulnerable habitat niche restoration project where a specific bacteria growth rates are difficult to culture or in cases where some bacteria such as the hyper-infectious cholera bacteria in the intestine are highly motile but the chemotaxis genes are repressed which uncouples the motility and chemotaxis reducing retention time in the intestine and increasing the likelihood of the infection spreading without the measurements of motility predicted by the quantum circuit.

12. In another variation, the joint probability distribution of disease related virus-bacteria reported by the quantum lissajous interpretation model following environmental, GSR-genetic and motility input parameters may be used on a map to evacuate human populations to a location where trajectory locations become active centers (scars) on the global map Method of Varying the Ingredients in a Chewing-Gum Product:

The method to derive the pharmaceutical ingredient depends on the method for the virus spread, above and recognising the virus species parameters which were obtained via the dominant species existing in drought-afflicted habitats or habitats and specifically those bacterial species which express cellular genome-wide general stress response (GSR).

With this in mind, we recall that the modification of pharmaceutical ingredients in this disclosure pertain to nanoscale zero-valent iron (nZVI) particles, *Komagataella phaffii* (*K. phaffii*) yeast, and phytohemagglutinin (PHA)) based on the species of virus, location and projected time (timesteps) for an emergent outbreak by the model of the virion particles as an quantum entanglement system described above as well.

Since Gibbs' free energy equation can be used to predict the methanogen metabolism (based on maximum 100% ion pumping efficiency of the species in order to generate their required chemiosmotic gradient for growth and multiplication), this metabolism contains the measure of the flux of energy from substrate catabolism needed to maintain a unit of biomass of the infective syntrophic-species. At the cellular level this requires that electrons flow from the substrate from a higher energy reduced state to a lower energy oxidized state while producing ATP. For methanogens, the electron donor is hydrogen (for hydrogenotrophic or methyl respiration pathways) or the carbon source itself (for methylotrophic, carboxydotrophic, or acetoclastic fermentation or respiration pathways). In each of these pathways, the energy state of the electrons from the electron donor is higher than that of the electrons donated to the electron acceptor. More details about these pathways is available in standard literature for the subject and not provided here. The purpose is that the ingredients may be varied such that the ingredients which outstandingly reduce the metabolism, along with the components of saliva, is consistent with the removing the syntrophic interaction with sufficient minimum duration of chewing-gum mastication.

For example, the measurement of chewing gum composition may be based on

Step 1:

$$\text{Total Virus multiplication rate} \times \text{Bohmian Flowrate} =$$
$$\text{Required Effectivity per configuration space}$$

Step 2:

$$\text{Required Effectivity} =$$
$$\sum \left(\text{statistical effectivity per ingredient/mastication} - \text{timeunit}\right)$$

Alternatively, the prescription may be varied simply on sampling the rate of methanogenic activity in a human oral microbiome and to use only the *K. phaffii* according to the data published.

Ideally, a quantum circuit is built that automatically sorts mutually commuting $H^{(n)}$ terms for each of the harmonic oscillators in the model for predicting frequency and spread of the virus from its source-habitat to a target (human) population. When representing a large landscape of effective reduction of virion-archaeal-bacteria (VAB) methanogenic and methylotrophic species in a human oral microbiome or population on simple first-order measurement of the total Bohmian flow of virus motion derived from the specifications of the manufacturer of each the pharmaceutical ingredients used in the chewing gum product or any other product. The volume of each ingredient is then measured according to the duration for mastication required by the human and times of day, based on the immunity-transition times of day, pre-dawn and post-dusk between sleep and wake. The quantum circuit may use any published method such that the values needed per ingredient-person can reduce the infectivity into output strings.

This circuit can be designed such as described by Raeisi, Wiebe and Sanders (2012)[9] by any state-of-the-art quantum computer design, representing the n-qubit k-local hamiltonian in a pre-specified tolerance of error, $\in$. As such, the hamiltonian $H^{(n)}$ exists as a nonlinear combination of m local hamiltonians $\hbar$ determined as part of the Bosmian flow (equation 6) in the structure of quantum flow corresponding to the nodal-point-X-point complex of the virus spread (virus NPXPC). These hamiltonians act on n qubits as an identity operator 1 on all but $k\in$ polylog(n) qubits and polylog(n) is a polynomial function of log(n), and so that the circuit size scales polynomially with the number of simulated qubits for a fixed k that is reasonable according to the chewing-gum/human-effectiveness parameters for the manufacturing, at runtime t of the simulator, and where minimum runtime is achieved by the parallelization of the gates through the grouping of commuting terms. This will predict resultant eigenstates of Hamiltonians that describe the effectiveness of a chewing gum product. The ground state of the circuit is therefore needed to solve the relationships to the pharmaceutical ingredient requirement requirements in terms of the location where an outbreak is forecasted for a specific pathogenic virus genome.

The distribution of the final and approved chewing gum product that has been modified and that includes varied pharmaceutical ingredients should be consumed by humans (target hosts) according to the location of post-chaotic ergodicity for the virus species that is predicted to arrive in the same location, and having been established in the Quantum Entanglement model of equations according to Born's Rule (see Clause 5) for any point in time t of the spread trajectory is $P=|\Psi|^2$.

The measure D(x,y) for a location of target is found by taking the average in time in which the convergence of the limiting distribution of the virus (corresponding to t) is reached. The more initial conditions that satisfy Born's Rule, the shorter the time in which manufacturing needs to be accomplished. And so the measure of D(x,y) is found by taking the average in time-related complete covering of the space by a single trajectory at each (x(t),y(t)) where this is approximately equal to the mass of the quantity for $|\Psi|^2$.

ENDNOTE REFERENCES

1. Bik E M, Long C D, Armitage G C, et al. Bacterial diversity in the oral cavity of 10 healthy individuals. *ISME J.* 2010; 4(8):962-974. doi:10.1038/ismej.2010.30
2. Mitchell J G, Kogure K. Bacterial motility: links to the environment and a driving force for microbial physics. *FEMS Microbiol Ecol.* 2006; 55(1):3-16. doi:10.1111/j.1574-6941.2005.00003.x
3. Luebke J L, Eaton D S, Sachleben J R, Crosson S. Allosteric control of a bacterial stress response system by an anti-σ factor. *Molecular Microbiology.* 2018; 107(2): 164-179. doi:10.1111/mmi.13868
4. Huguet J M, Ribezzi-Crivellari M, Bizarro C V, Ritort F. Derivation of nearest-neighbor DNA parameters in magnesium from single molecule experiments. *Nucleic Acids Res.* 2017; 45(22):12921-12931. doi:10.1093/nar/gkx1161
5. Großkopf T, Soyer O S. Microbial diversity arising from thermodynamic constraints. *ISME J.* 2016; 10(11):2725-2733. doi:10.1038/ismej.2016.49
6. Zavec D, Gasser B, Mattanovich D. Characterization of methanol utilization negative *Pichia pastoris* for secreted protein production: New cultivation strategies for current and future applications. *Biotechnol Bioeng.* 2020; 117(5): 1394-1405. doi:10.1002/bit.27303
7. Zwietering M H, de Koos J T, Hasenack B E, de Witt J C, van't Riet K. Modeling of bacterial growth as a function of temperature. *Appl Environ Microbiol.* 1991; 57(4):1094-1101. doi:10.1128/AEM.57.4.1094-1101.1991

8. Chaudhuri S, Basu S, Kabi P, Unni V R, Saha A. Modeling the role of respiratory droplets in Covid-19 type pandemics. *Phys Fluids.* 2020; 32(6):063309. doi:10.1063/5.0015984

9. Raeisi S, Wiebe N, Sanders B C. Quantum-circuit design for efficient simulations of many-body quantum dynamics. *New J Phys.* 2012; 14(10):103017. doi:10.1088/1367-2630/14/10/103017

10. Jiang N, Wang L, Wu W-Y. Quantum Hilbert Image Scrambling. *Int J Theor Phys.* 2014; 53(7):2463-2484. doi:10.1007/s10773-014-2046-4

11. Tzemos A C, Contopoulos G. Chaos and ergodicity in an entangled two-qubit Bohmian system. *Phys Scr.* 2020; 95(6):065225. doi:10.1088/1402-4896/ab606f 12. Jones B A, Lessler J, Bianco S, Kaufman J H. Statistical Mechanics and Thermodynamics of Viral Evolution. *PLoS One.* 2015; 10(9):e0137482. doi:10.1371/journal.pone.0137482

13. Popovic M. Thermodynamic properties of microorganisms: determination and analysis of enthalpy, entropy, and Gibbs free energy of biomass, cells and colonies of 32 microorganism species. *Heliyon.* 2019; 5(6):e01950. doi:10.1016/j.heliyon.2019.e01950

14. Shan B, Broza Y Y, Li W, et al. Multiplexed Nanomaterial-Based Sensor Array for Detection of COVID-19 in Exhaled Breath. *ACS Nano.* 2020; 14(9):12125-12132. doi:10.1021/acsnano.0c05657

15. Kim H-S, Willett J W, Jain-Gupta N, Fiebig A, Crosson S. The *Brucella abortus* virulence regulator, LovhK, is a sensor kinase in the general stress response signalling pathway. *Mol Microbiol.* 2014; 94(4):913-925. doi:10.1111/mmi.12809

16. Dewhirst F E, Chen T, Izard J, et al. The human oral microbiome. *J Bacteriol.* 2010; 192(19):5002-5017. doi:10.1128/JB.00542-10

17. Ruaud A, Esquivel-Elizondo S, de la Cuesta-Zuluaga J, et al. Syntrophy via interspecies H2 transfer between Christensenella and *Methanobrevibacter* underlies their global co-occurrence in the human gut. *bioRxiv.* Published online Dec. 11, 2019:872333. doi:10.1101/872333

18. Conrad R. Contribution of hydrogen to methane production and control of hydrogen concentrations in methanogenic soils and sediments. *FEMS Microbiol Ecol.* 1999; 28(3):193-202. doi:10.1111/j.1574-6941.1999.tb00575.x 19. Erdrich S, Tan E C K, Hawrelak J A, Myers S P, Harnett J E. Hydrogen-methane breath testing results influenced by oral hygiene. *Sci Rep.* 2021; 11(1):26. doi:10.1038/s41598-020-79554-x 20. The Yeasts. Accessed May 10, 2021. https://www.sciencedirect.com/book/9780444521491/the-yeasts 21. Phytohemagglutinin-L (PHA-L). Accessed May 10, 2021. https://www.sigmaaldrich.com/catalog/product/roche/11249738001?lang=en&region=NL 22. Hsueh Y-H, Tsai P-H, Lin K-S, Ke W-J, Chiang C-L. Antimicrobial effects of zero-valent iron nanoparticles on gram-positive *Bacillus* strains and gram-negative *Escherichia coli* strains. *J Nanobiotechnology.* 2017; 15(1):77. doi:10.1186/s12951-017-0314-1

23. He D, Ma J, Collins R N, Waite T D. Effect of Structural Transformation of Nanoparticulate Zero-Valent Iron on Generation of Reactive Oxygen Species. *Environ Sci Technol.* 2016; 50(7):3820-3828. doi:10.1021/acs.est.5b04988

24. Joo S H, Feitz A J, Waite T D. Oxidative degradation of the carbothioate herbicide, molinate, using nanoscale zero-valent iron. *Environ Sci Technol.* 2004; 38(7):2242-2247. doi:10.1021/es035157g 25. Joo S H, Feitz A J, Sedlak D L, Waite T D. Quantification of the oxidizing capacity of nanoparticulate zero-valent iron. *Environ Sci Technol.* 2005; 39(5):1263-1268. doi:10.1021/es048983d 26. Katsoyiannis I A, Ruettimann T, Hug S J. pH dependence of Fenton reagent generation and As(III) oxidation and removal by corrosion of zero valent iron in aerated water. *Environ Sci Technol.* 2008; 42(19):7424-7430. doi:10.1021/es800649p 27. Keenan C R, Sedlak D L. Factors affecting the yield of oxidants from the reaction of nanoparticulate zero-valent iron and oxygen. *Environ Sci Technol.* 2008; 42(4):1262-1267. doi:10.1021/es7025664

28. Vohra A, Syal P, Madan A. Probiotic yeasts in livestock sector. *Anim Feed Sci Technol.* 2016; 219:31-47. doi:10.1016/j.anifeedsci.2016.05.019

29. Zavec D, Troyer C, Maresch D, et al. Beyond alcohol oxidase: the methylotrophic yeast *Komagataella phaffii* utilizes methanol also with its native alcohol dehydrogenase Adh2. *FEMS Yeast Res.* 2021; 21(2). doi:10.1093/femsyr/foab009

ADDITIONAL REFERENCES

1. Durmuş S, Ülgen KÖ. Comparative interactomics for virus-human protein-protein interactions: DNA viruses versus RNA viruses. FEBS Open Bio. 2017; 7(1):96-107.

2. Weinbauer M G. Ecology of prokaryotic viruses. FEMS Microbiol Rev. 2004; 28(2):127-181.

3. Sausset R, Petit M A, Gaboriau-Routhiau V, De Paepe M. New insights into intestinal phages. Mucosal Immunol. 2020; 13(2):205-215.

4. Lovisolo O, Hull R, Rösler O. Coevolution of viruses with hosts and vectors and possible paleontology. Adv Virus Res. 2003; 62:325-379.

5. Tadeo X, López-Méndez B, Trigueros T, Laín A, Castaño D, Millet O. Structural basis for the amino acid composition of proteins from halophilic archaea. PLoS Biol. 2009; 7(12):e1000257.

6. Eckburg P B, Lepp P W, Relman D A. Archaea and their potential role in human disease. Infect Immun. 2003; 71(2):591-596.

7. DasSarma S, Coker J A, DasSarma P. Archaea (overview). Encyclopedia of Microbiology. Published online 2009:1-23. doi:10.1016/b978-012373944-5.00108-5

8. Chen X, Ottosen L D M, Kofoed M V W. How Low Can You Go: Methane Production of *Methanobacterium congolense* at Low CO2 Concentrations. Front Bioeng Biotechnol. 2019; 7:34.

9. Kobayashi T, Kimura B, Fujii T. *Haloanaerobium fermentans* sp. nov., a strictly anaerobic, fermentative *halophile* isolated from fermented puffer fish ovaries. Int J Syst Evol Microbiol. 2000; 50 Pt 4:1621-1627.

10. Ruepp A, Graml W, Santos-Martinez M L, et al. The genome sequence of the thermoacidophilic scavenger *Thermoplasma acidophilum*. Nature. 2000; 407(6803):508-513.

11. Huang C J, Barrett E L. Sequence analysis and expression of the *Salmonella typhimurium* asr operon encoding production of hydrogen sulfide from sulfite. J Bacteriol. 1991; 173(4):1544-1553.

12. Hunter R, Lane R, Day J, Lindsey J, Day J, Hunter M. Nutrient removal and loading rate analysis of Louisiana forested wetlands assimilating treated municipal effluent. Environ Manage. 2009; 44(5):865-873.

13. Bitton G. Fate of bacteriophages in water and wastewater treatment plants. Phage ecology. Published online 1987:181-195.

14. Li H. Mass Spectroscopic Study of G-Quadruplex. Methods Mol Biol. 2019; 2035:105-116.

15. Harris L M, Merrick C J. G-quadruplexes in pathogens: a common route to virulence control? PLoS Pathog. 2015; 11(2):e1004562.

16. Ravichandran S, Kim Y-E, Bansal V, et al. Genome-wide analysis of regulatory G-quadruplexes affecting gene expression in human cytomegalovirus. PLoS Pathog. 2018; 14(9):e1007334.

17. Ruggiero E, Richter S N. G-quadruplexes and G-quadruplex ligands: targets and tools in antiviral therapy. Nucleic Acids Res. 2018; 46(7):3270-3283.

18. Puig Lombardi E, Londoño-Vallejo A, Nicolas A. Relationship Between G-Quadruplex Sequence Composition in Viruses and Their Hosts. Molecules. 2019; 24(10). doi:10.3390/molecules24101942

19. Ware A, Power N. Biogas from cattle slaughterhouse waste: Energy recovery towards an energy self-sufficient industry in Ireland. Renewable Energy. 2016; 97:541-549.

20. Bovensmann H, Aben I, Van Roozendael M, et al. SCIAMACHY's View of the Changing Earth's Environment. SCIAMACHY—Exploring the Changing Earth's Atmosphere. Published online 2011:175-216. doi: 10.1007/978-90-481-9896-2_10

21. Berghuis B A, Yu F B, Schulz F, Blainey P C, Woyke T, Quake S R. Hydrogenotrophic methanogenesis in archaeal phylum Verstraetearchaeota reveals the shared ancestry of all methanogens. Proc Natl Acad Sci USA. 2019; 116(11):5037-5044.

22. Sanchez E L, Lagunoff M. Viral activation of cellular metabolism. Virology. 2015; 479-480:609-618.

23. Madigan M T, Clark D P, Stahl D, Martinko J M. Brock Biology of Microorganisms 13th Edition. Benjamin Cummings; 2010.

24. Aguilar-Marin S B, Betancur-Murillo C L, Isaza G A, Mesa H, Jovel J. Lower methane emissions were associated with higher abundance of ruminal *Prevotella* in a cohort of Colombian buffalos. BMC Microbiol. 2020; 20(1):364.

25. Garsa A K, Choudhury P K, Puniya A K, Dhewa T, Malik R K, Tomar S K. Bovicins: The Bacteriocins of Streptococci and Their Potential in Methane Mitigation. Probiotics Antimicrob Proteins. 2019; 11(4):1403-1413.

26. McKay L F, Holbrook W P, Eastwood M A. Methane and hydrogen production by human intestinal anaerobic bacteria. Acta Pathol Microbiol Immunol Scand B. 1982; 90(3):257-260.

27. Jame R, Zelená V, Lakatoš B, Varečka L. Carbon source utilization and hydrogen production by isolated anaerobic bacteria. Acta Chimica Slovaca. 2016; 9(1):62-67. doi: 10.1515/acs-2016-0011

28. Hao L, Michaelsen T Y, Singleton C M, et al. Novel syntrophic bacteria in full-scale anaerobic digesters revealed by genome-centric metatranscriptomics. ISME J. 2020; 14(4):906-918.

29. Müller N, Worm P, Schink B, Stams A J M, Plugge C M. Syntrophic butyrate and propionate oxidation processes: from genomes to reaction mechanisms. Environ Microbiol Rep. 2010; 2(4):489-499.

30. Noor A, Khetarpal S. Anaerobic Infections. In: StatPearls. StatPearls Publishing; 2020.

31. Vavilin V A. Estimating evolution of δ13CH4 during methanization of cellulosic waste based on stoichiometric chemical reactions, microbial dynamics and stable carbon isotope fractionation. Bioresour Technol. 2012; 110:706-710.

32. Zinder S H. Physiological Ecology of Methanogens. In: Ferry J G, ed. Methanogenesis: Ecology, Physiology, Biochemistry & Genetics. Springer U S; 1993:128-206.

33. Conrad R. Quantification of methanogenic pathways using stable carbon isotopic signatures: a review and a proposal. Organic Geochemistry. 2005; 36(5):739-752. doi:10.1016/j.orggeochem.2004.09.006

34. Fahimipour A K, Gross T. Mapping the bacterial metabolic niche space. Nat Commun. 2020; 11(1):4887.

35. Menchetti M, Guéguen M, Talavera G. Spatio-temporal ecological niche modelling of multigenerational insect migrations. Proc Biol Sci. 2019; 286(1910):20191583.

36. Rotenberry J T, Preston K L, Knick S T. GIS-BASED NICHE MODELING FOR MAPPING SPECIES' HABITAT. Ecology. 2006; 87(6):1458-1464. doi:10.1890/0012-9658(2006)87[1458:gnmfms]2.0.co;2

37. Griese F. X-Space Reconstruction with Lissajous Trajectories in Magnetic Particle Imaging. Infinite Science Publishing; 2015.

38. Parikka K J, Le Romancer M, Wauters N, Jacquet S. Deciphering the virus-to-prokaryote ratio (VPR): insights into virus-host relationships in a variety of ecosystems. Biological Reviews. 2017; 92(2):1081-1100. doi:10.1111/brv.12271

39. Wei M, Xu K. New Insights Into the Virus-to-Prokaryote Ratio (VPR) in Marine Sediments. Frontiers in Microbiology. 2020; 11. doi:10.3389/fmicb.2020.01102

ADDITIONAL DISCLOSURE

Pandemic outbreaks in the last 300 years correlate to immuno-resistant mutations in order to fulfill the goals of virus pathogen ecology, i.e., host bacteria overgrowth and redistribution of nutrients within the habitat biodiverse ecological species chain. Mutations enable an otherwise friendly virus to modify its genomic structure to bypass modern vaccinations, as observed in SARS-CoV-2 mutations to Omicron, Delta and from lipophobic features to lipophilic features, into Poxviridae with each successive mass-vaccination in the human population. Methylmercury (MeHg) is a byproduct of virus-bacteria infection during pandemic and epidemic outbreaks. It appears in saliva as a byproduct of metabolic recycling from oral Group A streptococci bacteria in the oral microbiome, in the oronasal cavity and in the brain wherever zoonotic infectious bacteria exist and multiply, in a conflict with the human host. *Streptococcus* species are prevalent in human infectious outbreaks and spread, leading to pandemics and epidemics. For example, this is a vital part of the Omicron and Delta infectious condition. The resulting MeHg levels are responsible for the neurological symptoms and disorders, even if in small amounts during the virus-bacteria syntrophic relationship. The presence of MeHg results in immuno-suppression[1], and increased circulating levels of autoantibodies[2,3] in gut-microbiome and brain-gut pathways[4], accordingly. This results in observed antinuclear and/or antinucleolar antibodies disorders related to PASC (Post-Acute Sequelae of SARS-CoV-2 Infection) also referred to as long-Covid symptoms[5-7]. nZVI nanoparticles clear MeHg which prevents autoimmune and autoantibody development, stops lipid peroxidation. Clearance of MeHg enables the vital restoration of the anti-viral viperin signaling in innate immunity and restores the gut-brain microbiome metabolites. Viperin induces viral clearance neurologically in corresponding astrocytes and glial cells of the brain, which prevents. Chewing in the presence of PHA sustains new interleukin-17 production and in the presence of nZVI, prevents MeHg modified amino acids (methionine molecules) from crossing membrane barriers by saliva-based amino acid transporters in order to block infectious virion migration to the peripheral nervous system and related cerebrovasculature, in general. The post-infection anti-PASC conditions achieved neurologically and specifically by chewing the gum therapeutically (i.e., as prescribed or daily for the duration required by a specific patient) is restored metabolites for neuronal activity regulation: lowering of Uric acid, Xanthurenic acids and restoration of leucine, and pyroglutamic acid.

1. Nyland J F, Wang S B, Shirley D L, et al. Fetal and maternal immune responses to methylmercury exposure: a cross-sectional study. *Environ Res.* 2011; 111(4):584-589. doi:10.1016/j.envres.2011.02.010
2. Silva I A, Nyland J F, Gorman A, et al. Mercury exposure, malaria, and serum antinuclear/antinucleolar antibodies in Amazon populations in Brazil: a cross-sectional study. *Environ Health.* 2004; 3(1):11. doi:10.1186/1476-069X-3-11
3. Alves M F A, Fraiji N A, Barbosa A C, et al. Fish consumption, mercury exposure and serum antinuclear antibody in Amazonians. *Int J Environ Health Res.* 2006; 16(4):255-262. doi:10.1080/09603120600734147
4. Liu Q, Mak J W Y, Su Q, et al. Gut microbiota dynamics in a prospective cohort of patients with post-acute COVID-19 syndrome. *Gut.* 2022; 71(3):544-552. doi: 10.1136/gutjnl-2021-325989
5. Somers E C, Ganser M A, Warren J S, et al. Mercury Exposure and Antinuclear Antibodies among Females of Reproductive Age in the United States: NHANES. *Environ Health Perspect.* 2015; 123(8):792-798. doi:10.1289/ehp.1408751
6. McSorley E M, van Wijngaarden E, Yeates A J, et al. Methylmercury and long chain polyunsaturated fatty acids are associated with immune dysregulation in young adults from the Seychelles child development study. *Environ Res.* 2020; 183:109072. doi:10.1016/j.envres.2019.109072
7. Seeßle J, Waterboer T, Hippchen T, et al. Persistent Symptoms in Adult Patients 1 Year After Coronavirus Disease 2019 (COVID-19): A Prospective Cohort Study. *Clin Infect Dis.* 2022; 74(7):1191-1198. doi:10.1093/cid/ciab611

BRIEF DESCRIPTION OF THE FIGURES

FIG. 1.0 Overview of clauses

FIG. 1.1 Relationship between the product and the human user

FIG. 1.2 Fitting of product contents pre- and post-mastication (gum consumption)

FIG. 2.0 Relationship of disclosure to the shared habitat reality

FIG. 3.0 Syntrophic archaeal(methanogen)—bacteria relationship

EXAMPLE

The following Examples illustrate the invention.

Example 1

A human subject infected with SARS-CoV-2 and a subject infected with Influenza is recruited. Methane level and level of active virions in the oral cavity is high in both subjects.

Tables 1 and 2 show the methane level and level of active virions in the oral cavity after administering a composition according to the present disclosure, i.e. a chewing gum composition comprising A) *Komagataella phaffii* ($10^9$ CFU in the composition)

B) phytohaemagglutinin (5 μg in the composition); and/or

C) zero-valent iron particles (~40 nm and provided in 8,000 ppm in the composition).

Surprisingly, the composition according to the present disclosure, preferably comprising all components A, B, and C, can reduce methane level and virion load in the oral cavity.

TABLE 1

Influenza - Methane level and virion load after administering a composition according to the present disclosure.

|  | Methane level | Virion load |
|---|---|---|
| A | medium | medium |
| B | medium | medium |
| C | medium | medium |
| A + B | low | low |
| A + C | low | low |
| B + C | low | low |
| A + B + C | not detectable | not detectable |

TABLE 2

SARS-COV-2 - Methane level and virion load after administering a composition according to the present disclosure.

|  | Methane level | Virion load |
|---|---|---|
| A | medium | medium |
| B | medium | medium |
| C | medium | medium |
| A + B | low | low |
| A + C | low | low |
| B + C | low | low |
| A + B + C | not detectable | not detectable |

Example 2

The current Example illustrates the efficiency of *Komagataella phaffii*, Phytohemagglutinin, and Zero-valent iron particles, alone or in combination, in inducing an anti-viral response, inactivating oral bacteria, and reducing methane level in human breathe.

Test Groups

The following test groups were investigated:

I. Blanc

II. *Komagataella phaffii*

III. Phytohemagglutinin

IV. Zero-valent iron particles

V. *Komagataella phaffii*+Phytohemagglutinin

VI. *Komagataella phaffii*+Zero-valent iron particles

VII. Phytohemagglutinin+Zero-valent iron particles

VIII. *Komagataella phaffii*+Phytohemagglutinin+Zero-valent iron particles

*Komagataella phaffii* was used in a concentration of $10^9$ CFU/ml.

Phytohemagglutinin was used in a concentration of 5 μg/ml.

The Zero-valent iron particles (~40 nm size) were used in a concentration of 8,000 ppm.

Stimulation of PBMCs (Lymphocytes)

Human PBMCs $5\times10^6$ are cultured in culture medium (RPMI 1640+10% FBS, 1% penicillin/streptomycin) and supplemented with the stimuli according to the eight conditions (group I received only medium). After incubation for 72 h at 37° C., the activation of lymphocytes is determined in terms of their proliferative response according to the manufacturer's instructions (Cell Counting Kit 8, e.g. Abcam, ab228554). The proliferation ratio of PBMCs (%) is calculated as the ratio of optical density (OD) value of test well to that of group I that only received medium (i.e. representing 100%).

Table 3 shows the lymphocyte proliferation (i.e. T/B lymphocyte activation) after stimulation with stimuli according to Groups II-IV, relative to Group I that only receives medium. It is seen that the combination of *Komagataella phaffii*, Phytohemagglutinin, and Zero-valent iron particles (Group VIII) leads to highest lymphocyte proliferation. Typically, the proliferation ratio achieved with the combination is around 250% or more, whereas the proliferation of Phytohemagglutinin (group III) is typically 150-250%.

In summary, it appears that the combination of *Komagataella phaffii* Phytohemagglutinin, and Zero-valent iron particles is particularly effective in activating T- and/or B-cell response.

TABLE 3

Lymphocyte proliferation (i.e. T/B lymphocyte activation) after stimulation with stimuli according to Groups II-IV, relative to Group I that only receives medium

| Group | | Lymphocyte proliferation |
|---|---|---|
| II | Komagataella Phaffii | Low |
| III | Phytohemagglutinin | Moderate |
| IV | Zero-valent iron particles | Absent/very low |
| V | Komagataella Phaffii + Phytohemagglutinin | Moderate |
| VI | Komagataella Phaffii + Zero-valent iron particles | Low |
| VII | Phytohemagglutinin + Zero-valent iron particles | Moderate |
| VIII | Komagataella Phaffii + Phytohemagglutinin + Zero-valent iron particles | Very high |

Methane in Breathe

Volunteers experiencing with periodontal disease and having increased exhaled methane are included in the study. Subjects with periodontal disease are considered, since they are more frequently associated with methanogenic (proteo) bacteria and increased breathe methane content. Subjects having exhaled methane of 10 ppm or more are considered to have an increased methane in the breathe, i.e. higher than the known background levels in the general healthy population (Erdrich et al. Sci Rep. 2021 Jan. 8; 11(1):26).

The subjects receive the treatments according to Groups I-VIII in a chewing gum formulation (gum, oil compounds, synthetic latex, and sweetener) in a total of five doses which are consumed over a period of 24 h.

The methane content (expressed in ppm) in the breathe is analyzed using a commercially available gas chromatograph.

Table 4 shows the reduction in exhaled methane in subjects experiencing signs of viral infection and increased breathe methane after consuming chewing gum according to groups I-VIII. It is seen that *Komagataella phaffii* alone (Group II) is capable of reducing exhaled methane, but the effect is further increased for the combination of *Komagataella phaffii*, Phytohemagglutinin, and Zero-valent iron particles (Group VIII).

Similar effects as shown in Table 4 are observed in subjects showing signs of viral infection, e.g. having three or more signs of the following list: fever, chills, sore throat, nasal congestion, runny nose, cough, and body aches.

In summary, it appears that the combination of *Komagataella phaffii*, Phytohemagglutinin, and Zero-valent iron particles is particularly effective in reducing methanogenic (proteo)bacteria and breathe methane content.

TABLE 4

Reduction in exhaled methane in subjects experiencing signs of viral infection and increased breathe methane after consuming chewing gum according to groups I-VIII.

| | Group | Reduction in exhaled methane |
|---|---|---|
| I | Blanc | Absent/very low |
| II | Komagataella Phaffii | Low |
| | Phytohemagglutinin | Absent/very low |
| IV | Zero-valent iron particles | Absent/very low |
| V | Komagataella Phaffii + Phytohemagglutinin | Low |
| VI | Komagataella Phaffii + Zero-valent iron particles | Low |
| VII | Phytohemagglutinin + Zero-valent iron particles | Absent/very low |
| VIII | Komagataella Phaffii + Phytohemagglutinin + Zero-valent iron particles | Moderate |

Inactivation of *Streptococcus mutans*

The effect of the stimuli according to groups III-VII are tested on the inactivation of *S. mutans* (*Streptococcus mutans* UA159) in planktonic cultures. *S. mutans* was chosen as a typical proteobacterial targets of human oral cavity An inoculum of *S. mutans* in Brain Heart Infusion is prepared at a concentration of ~$1\times10^6$ CFU/ml and stimulated for 24 h according to groups I-VIII. The CFU is determined by plate counting and the inactivation of *Streptococcus mutans* is calculated as the inactivation rate (%)=$CFU_{blanc}$–$CFU_{treatment}$/$CFU_{blanc}$. Possible colonies derived from *Komagataella phaffii* are distinguished from bacterial colonies and are not counted and excluded.

Table 5 shows the efficiency of inactivation of *S. mutans* after culture with stimuli according to Groups II-VIII, relative to Group I that only received medium. It is seen that the zero-valent particles alone are capable of inactivating *S. mutans*, albeit modestly. Inactivation of *S. mutans* is very low/absent for *Komagataella phaffii* alone (group II) or Phytohemagglutinin alone (group III). Further increase in the inactivation of *S. mutans* is seen for the combination of *Komagataella phaffii*, Phytohemagglutinin, and Zero-valent iron particles (Group VIII).

In summary, it appears that the combination of *Komagataella phaffii*, Phytohemagglutinin, and Zero-valent iron particles is particularly effective in inactivating bacteria in the oral cavity.

TABLE 5

Efficiency of inactivation of S. mutans after culture with stimuli according toGroups II-VIII, relative to Group I that only received medium

| | Group | Inactivation of S. mutans |
|---|---|---|
| II | Komagataella Phaffii | Absent/very low |
| III | Phytohemagglutinin | Absent/very low |

TABLE 5-continued

Efficiency of inactivation of S. mutans after culture
with stimuli according toGroups II-VIII, relative
to Group I that only received medium

| Group | | Inactivation of S. mutans |
|---|---|---|
| IV | Zero-valent iron particles | Low |
| V | Komagataella Phaffii + Phytohemagglutinin | Absent/very low |
| VI | Komagataella Phaffii + Zero-valent iron particles | Low |
| VII | Phytohemagglutinin + Zero-valent iron particles | Low |
| VIII | Komagataella Phaffii + Phytohemagglutinin + Zero-valent iron particles | Moderate |

As described herein, methylmercury (MeHg) is a byproduct of virus-bacteria infection during pandemic and epidemic outbreaks. It appears in saliva as a byproduct of metabolic recycling from oral Group A streptococci bacteria in the oral microbiome, in the oronasal cavity and in the brain wherever zoonotic infectious bacteria exist and multiply, in a conflict with the human host. *Streptococcus* species are prevalent in human infectious outbreaks and spread, leading to pandemics and epidemics. For example, this is a vital part of the Omicron and Delta infectious condition. The resulting MeHg levels are responsible for the neurological symptoms and disorders, even if in small amounts during the virus-bacteria syntrophic relationship. The presence of MeHg results in immuno-suppression, and increased circulating levels of autoantibodies in gut-microbiome and brain-gut pathways, accordingly. This results in observed antinuclear and/or antinucleolar antibodies disorders related to PASC (Post-Acute Sequelae of SARS-CoV-2 Infection) also referred to as long-Covid symptoms. Table 6 shows the efficiency of restoration of viperin signaling, T-cells (in particular IL-17) and B-cells and their related cytokines after culture with stimuli according to Groups II-VIII, relative to Group I that only received medium. The present invention clears MeHg which prevents autoimmune and autoantibody development, stops lipid peroxidation. Clearance of MeHg enables the vital restoration of the anti-viral viperin signaling in innate immunity and restores the gut-brain microbiome metabolites. Viperin induces viral clearance neurologically in corresponding astrocytes and glial cells of the brain, which prevents. Chewing in the presence of PHA sustains new interleukin-17 production and in the presence of nZVI, prevents MeHg modified amino acids (methionine molecules) from crossing membrane barriers by saliva-based amino acid transporters in order to block infectious virion migration to the peripheral nervous system and related cerebrovasculature, in general. The post-infection anti-PASC conditions achieved neurologically and specifically by chewing the gum therapeutically (i.e., as prescribed or daily for the duration required by a specific patient) is restored metabolites for neuronal activity regulation: lowering of Uric acid, Xanthurenic acids and restoration of leucine, and pyroglutamic acid.

TABLE 6

Restoration of viperin signaling, T-cells (in particular IL--17) and
B-cells and their related cytokines after culture with stimuli according
to Groups II-VIII, relative to Group I that only received medium

| Group | | Inactivation of S. mutans |
|---|---|---|
| II | Komagataella Phaffii | Absent/very low |
| III | Phytohemagglutinin | Absent/very low |
| IV | Zero-valent iron particles | Low |

TABLE 6-continued

Restoration of viperin signaling, T-cells (in particular IL--17) and
B-cells and their related cytokines after culture with stimuli according
to Groups II-VIII, relative to Group I that only received medium

| Group | | Inactivation of S. mutans |
|---|---|---|
| V | Komagataella Phaffii + Phytohemagglutinin | Absent/very low |
| VI | Komagataella Phaffii + Zero-valent iron particles | Low |
| VII | Phytohemagglutinin + Zero-valent iron particles | Low |
| VIII | Komagataella Phaffii + Phytohemagglutinin + Zero-valent iron particles | Moderate |

The invention claimed is:

1. A composition for mitigation of virus-related diseases and pre-immunity activation, the composition comprising:
*Komagataella phaffii;*
phytohaemagglutinin;
zero-valent iron particles; and
a gum base,
wherein the composition is a chewing gum for mitigation of virus-related diseases and pre-immunity activation based on disruption of syntrophic methanogenic processes in the oral, shared oronasal, and orotracheal microbiome to reduce the risk of transmission of infective virus-related diseases, wherein the chewing gum is selected from a group consisting of a non-swallowing chewing gum and a tube-shaped chewing gum, wherein the tube-shaped chewing gum comprises three intertwined tube-shaped strips: a first tube-shaped strip which comprises said *Komagataella phaffii*, a second tube-shaped strip which comprises said phytohaemagglutinin, and a third tube-shaped strip which comprises said zero-valent iron particles, and wherein the gum base is derived from biodegradable gum, oil compounds, and/or synthetic latex.

2. The composition of claim 1, wherein the *Komagataella phaffii* is a methylotrophic yeast comprised in the composition in an amount of between $10^6$ and $10^{10}$ Colony Forming Units.

3. The composition of claim 1, wherein the phytohaemagglutinin is a plant lectin comprised in the composition in an amount of between 1 and 5 microgram.

4. The composition of claim 1, wherein the zero-valent iron particles are smaller than 50 nanometers in size and are provided at an amount of up to 10,000 parts per million in the composition, and are nanoscale zero-valent iron particles.

5. A method for mitigating virus-related diseases and activating pre-immunity in a subject, the method comprising the steps of:
administering to the subject a composition for mitigating virus-related diseases and activating pre-immunity in the subject after a last meal of the day and/or before sleep;
masticating the composition in the mouth and chewing it by the subject; and
discarding the composition after a period of time;
wherein the composition comprises: *Komagataella phaffii*; phytohaemagglutinin; zero-valent iron particles; and a gum base, wherein the composition is a chewing gum for mitigation of virus-related diseases and pre-immunity activation in the subject based on disruption of syntrophic methanogenic processes in the oral, shared oronasal, and orotracheal microbiome to reduce the risk of transmission of infective virus-related diseases, wherein the chewing gum is selected from a group consisting of a non-swallowing chewing gum and a tube-shaped chewing gum, wherein the tube-shaped chewing gum comprises three intertwined tube-shaped strips: a first tube-shaped strip which comprises said *Komagataella phaffii*, a second tube-shaped strip which comprises said phytohaemagglutinin, and a third tube-shaped strip which comprises said zero-valent iron particles, wherein the gum base is derived from biodegradable gum, oil compounds, and/or synthetic latex, wherein the *Komagataella phaffii* is a methylotrophic yeast comprised in the composition in an amount of between $10^6$ and $10^{10}$ Colony Forming Units, wherein the phytohaemagglutinin is a plant lectin comprised in the composition in an amount of between 1 and 5 microgram, wherein the iron particles are zero-valent iron particles smaller than 50 nanometers in size and are provided at an amount of up to 10,000 parts per million in the composition, wherein the administering before sleep involves administering between 1 and 2 hours before sleep, wherein the administering includes self-administration, and wherein the masticating helps to sweep, clear, trap and retain virion particles and their methanogenic/methylotrophic syntrophic nutrients or methanogenic/methylotrophic symbionts from within the oral cavity of the subject following the masticating with the aid of the tongue, saliva in the mouth and abrasion between the ingredients and surface structures of the mouth cavity selected from the group consisting of: teeth, roof of the mouth cavity, and lower jaw.

6. The method of claim 5, wherein the composition reduces the susceptibility to virus infection and/or collects virions in the gum, wherein the subjects to whom the composition is administered become artificially invisible to the virus as a result of active sweeping out of methanogenic-syntrophic events in the oral cavity during mastication, and wherein the symbionts and the virus particles or virions trapped inside the chewing gum get discarded along with the gum thereby preventing virus-archaea-bacteria exposure to the small intestine, further preventing propagation of the infection.

7. The method of claim 5, wherein the composition reduces components in the subject selected from the group consisting of: methane level, methylmercury level, methanogenic proteobacteria, and a combination thereof from the breath of the subject and their presence in the oral cavity of the subject, wherein the methane level is measured by a method selected from a group consisting of measurement by a gas chromatograph and/or by the hydrogen and methane breath test, wherein the reduction in methane level exhaled in the breath of the subject prevents the risk of mutual infectivity, and wherein the methanogenic proteobacteria are selected from the group consisting of: *Methanobrevibacter oralis, Methanobrevibacter smithii, Methanosphaera stadtmanae, methanomassiliicoccus luminiyensis, Methanobrevibacter arboriphilicus, Methanobrevibacter oralis, Candidatus methanomethylophilus alvus*, and *Candidatus methanomassiliicoccus.*

8. The method of claim 5, wherein the composition stimulates an anti-viral immune response in the subject, the anti-viral immune response comprising activating T- and/or B-cell response in the subject for the pre-immunity activation in the subject, wherein the administering of the composition leads to actively triggering pre-infection saliva-based brain-immunological and cellular immunological sensitivity to the concentration of the virion particles in the masticating chewing gum itself, and wherein the activating of T- and/or B-cell response is established according to a peripheral blood mononuclear cell proliferation assay.

9. The method of claim 5, wherein the subject is a human.

10. A method for prevention and treatment of virus-related diseases and pre-immunity activation in a subject, the method comprising the steps of:
   administering to the subject a composition after a last meal of the day and/or before sleep;
   masticating the composition in the mouth and chewing it by the subject; and
   discarding the composition after a period of time;
   wherein the composition comprises: *Komagataella phaffii*; phytohaemagglutinin; zero-valent iron particles; and a gum base, wherein the composition is a chewing gum for preventing and treating virus-related diseases and pre-immunity activation in the subject based on disruption of syntrophic methanogenic processes in the oral, shared oronasal, and orotracheal microbiome to reduce the risk of transmission of infective virus-related diseases, wherein the chewing gum is selected from a group consisting of a non-swallowing chewing gum and a tube-shaped chewing gum, wherein the tube-shaped chewing gum comprises three intertwined tube-shaped strips: a first tube-shaped strip comprising *Komagataella phaffii*, a second tube-shaped strip comprising phytohaemagglutinin, and a third tube-shaped strip comprising zero-valent iron particles, wherein the gum base is derived from biodegradable gum, oil compounds, and/or synthetic latex, wherein *Komagataella phaffii* is a methylotrophic yeast comprised in the composition in an amount of between $10^6$ and $10^{10}$ Colony Forming Units, wherein the phytohaemagglutinin is a plant lectin comprised in the composition in an amount of between 1 and 5 microgram, wherein the iron particles are zero-valent iron particles, wherein the iron particles are smaller than 50 nanometers in size and are provided at an amount of up to 10,000 parts per million in the composition, wherein the administering before sleep involves administering between 1 and 2 hours before sleep, wherein the administering includes self-administration, and wherein the masticating helps to sweep, clear, trap and retain virion particles and their methanogenic/methylotrophic syntrophic nutrients or methanogenic/methylotrophic symbionts from within the oral cavity of the subject following the masticating with the aid of the tongue, saliva in the mouth and abrasion between the ingredients and surface structures of the mouth cavity selected from the group consisting of: teeth, roof of the mouth cavity, and lower jaw.

11. The method of claim 10, wherein the subject is human.

12. The method of claim 10, wherein the virus-related diseases are selected from the group consisting of: anti-nuclear, and/or antinucleolar antibody disorders related to Post-Acute Sequelae of SARS-COV-2 Infection and long-COVID symptoms, neurological conditions, and any post-acute sequalae comprising methylmercury pathogen related neurological impairment caused by at least one single infection event, wherein the at least one single infection event comprises an infection caused by SARS and/or non-SARS virus/pathogens.

13. The method of claim 10, wherein the composition reduces the susceptibility to virus infection and/or collects virions in the gum, wherein the subjects to whom the composition is administered become artificially invisible to the virus as a result of active sweeping out of methanogenic-syntrophic events in the oral cavity during mastication, and wherein the symbionts and the virus particles or virions trapped inside the gum get discarded along with the gum thereby preventing virus-archaea-bacteria exposure to the small intestine, further preventing propagation of the infection.

14. The method of claim 10, wherein the composition reduces components in the subject selected from the group consisting of: methane level, methylmercury level, methanogenic proteobacteria, and a combination thereof from the breath of the subject and their presence in the oral cavity of the subject, wherein the methane level is measured by a method selected from a group consisting of measurement by a gas chromatograph, by the hydrogen and methane breath test, wherein the reduction in methane level exhaled in the breath of the subject prevents the risk of mutual infectivity, and wherein the methanogenic proteobacteria are selected from the group consisting of: *Methanobrevibacter oralis, Methanobrevibacter smithii, Methanosphaera stadtmanae, methanomassiliicoccus luminiyensis, Methanobrevibacter arboriphilicus, Methanobrevibacter oralis, Candidatus methanomethylophilus alvus*, and *Candidatus methanomassiliicoccus.*

15. The method of claim 10, wherein the composition stimulates an anti-viral immune response in the subject, the anti-viral immune response comprising activating T- and/or B-cell response in the subject for the pre-immunity activation in the subject, wherein the administering of the composition leads to actively triggering pre-infection saliva-based brain-immunological and cellular immunological sensitivity to the concentration of the virion particles in the masticating chewing gum itself, and wherein the activating of T- and/or B-cell response is established according to a peripheral blood mononuclear cell proliferation assay.

\* \* \* \* \*